US011341726B2

(12) United States Patent
Tsuda et al.

(10) Patent No.: US 11,341,726 B2
(45) Date of Patent: May 24, 2022

(54) INFORMATION PROCESSING APPARATUS, INFORMATION PROCESSING METHOD, AND INFORMATION PROCESSING SYSTEM

(71) Applicant: SEIKO EPSON CORPORATION, Tokyo (JP)

(72) Inventors: Atsunari Tsuda, Suwa (JP); Toshikazu Uchiyama, Chino (JP); Hitomi Wakamiya, Matsumoto (JP); Masahide Takano, Matsumoto (JP)

(73) Assignee: SEIKO EPSON CORPORATION, Tokyo (JP)

( * ) Notice: Subject to any disclaimer, the term of this patent is extended or adjusted under 35 U.S.C. 154(b) by 61 days.

(21) Appl. No.: 16/851,780

(22) Filed: Apr. 17, 2020

(65) Prior Publication Data
US 2020/0257485 A1 Aug. 13, 2020

Related U.S. Application Data

(63) Continuation of application No. 16/026,214, filed on Jul. 3, 2018, now Pat. No. 10,664,216, which is a
(Continued)

(30) Foreign Application Priority Data

Jul. 16, 2013 (JP) .............................. JP2013-147420
Mar. 28, 2014 (JP) .............................. JP2014-067406

(51) Int. Cl.
*G06T 19/00* (2011.01)
*G06T 3/40* (2006.01)
(Continued)

(52) U.S. Cl.
CPC .......... *G06T 19/006* (2013.01); *G06F 3/1423* (2013.01); *G06T 3/40* (2013.01);
(Continued)

(58) Field of Classification Search
CPC ...... G02B 2027/0141; G02B 2027/014; G02B 27/017; G06K 9/00671; G06F 3/012; G06F 19/3406; A61B 34/25; A61B 2090/502
See application file for complete search history.

(56) References Cited

U.S. PATENT DOCUMENTS 8,099,296 B2   1/2012  Mahesh et al.
8,681,073 B1 *  3/2014  Robbins ........... H04N 21/42202
                                               345/7
(Continued)

FOREIGN PATENT DOCUMENTS

DE   10 2010 052 244 A1   5/2012
EP        1 643 401 A1    4/2006
(Continued)

OTHER PUBLICATIONS

Sun, "Chapter 16 Operating Room Integration and Display Systems: Brief Review," Making Health Care Safer II: An Updated Critical Analysis of the Evidence for Patient Safety Practices, Mar. 2013, pp. 1-6.
(Continued)

*Primary Examiner* — Michelle L Sams
(74) *Attorney, Agent, or Firm* — Oliff PLC

(57) ABSTRACT

An information processing apparatus including a processor configured to detect a connection to each of a first and second image display apparatus, generate a first image based on first medical apparatus information acquired from a first medical apparatus and a second image based on second medical apparatus information acquired from a second medical apparatus, detect an object from an outside scene that is captured by both the first and second image display apparatuses, and acquire a first distance from the first image display apparatus to the object and a second distance from the second image display apparatus to the object. When the
(Continued)

first distance is smaller than the second distance, the processor causes the first image display apparatus to display the first image at a first size that is greater than a second size of the first image displayed at the second image display apparatus.

12 Claims, 18 Drawing Sheets

Related U.S. Application Data continuation of application No. 14/901,198, filed as application No. PCT/JP2014/003697 on Jul. 11, 2014, now Pat. No. 10,042,598.

(51) Int. Cl.
| | |
|---|---|
| G06F 3/14 | (2006.01) |
| G02B 27/01 | (2006.01) |
| A61B 90/50 | (2016.01) |
| A61B 34/00 | (2016.01) |
| G16H 40/63 | (2018.01) |
| G16H 20/40 | (2018.01) |

(52) U.S. Cl.
CPC ......... *A61B 34/25* (2016.02); *A61B 2090/502* (2016.02); *G02B 27/017* (2013.01); *G02B 27/0172* (2013.01); *G02B 2027/014* (2013.01); *G02B 2027/0138* (2013.01); *G02B 2027/0141* (2013.01); *G02B 2027/0178* (2013.01); *G16H 20/40* (2018.01); *G16H 40/63* (2018.01)

(56) References Cited

U.S. PATENT DOCUMENTS

| | | | |
|---|---|---|---|
| 2003/0023534 | A1 | 1/2003 | Kadambe |
| 2005/0160479 | A1 | 7/2005 | Kubota |
| 2005/0206583 | A1 | 9/2005 | Lemelson et al. |
| 2006/0044399 | A1 | 3/2006 | Fredlund et al. |
| 2006/0074711 | A1 | 4/2006 | Mahesh et al. |
| 2006/0082542 | A1 | 4/2006 | Morita et al. |
| 2006/0109237 | A1 | 5/2006 | Morita et al. |
| 2007/0184422 | A1 | 8/2007 | Takahashi |
| 2008/0058612 | A1 | 3/2008 | Ohyu et al. |
| 2009/0136223 | A1* | 5/2009 | Motomura ......... H04N 5/23212 396/77 |
| 2009/0326336 | A1 | 12/2009 | Lemke et al. |
| 2010/0045580 | A1 | 2/2010 | Ichikawa et al. |
| 2010/0245387 | A1 | 9/2010 | Bachelder et al. |
| 2010/0249540 | A1 | 9/2010 | Lisogurski |
| 2010/0299627 | A1 | 11/2010 | Kenagy |
| 2011/0055325 | A1 | 3/2011 | Kubota |
| 2011/0164163 | A1 | 7/2011 | Bilbrey et al. |
| 2011/0250962 | A1 | 10/2011 | Feiner et al. |
| 2012/0266225 | A1 | 10/2012 | Kubota |
| 2013/0093738 | A1 | 4/2013 | Manus et al. |
| 2013/0290882 | A1 | 10/2013 | Cotte |
| 2014/0082083 | A1 | 3/2014 | Kubota |

FOREIGN PATENT DOCUMENTS

| | | | |
|---|---|---|---|
| EP | 2 271 078 A2 | 1/2011 | |
| EP | 2 544 039 A1 | 1/2013 | |
| JP | 2001-104331 A | 4/2001 | |
| JP | 2005-208823 A | 8/2005 | |
| JP | 2006-102495 A | 4/2006 | |
| JP | 2008-234072 A | 10/2008 | |
| JP | 2010-259497 A | 11/2010 | |
| JP | 4762160 B2 | 8/2011 | |
| JP | 2012186659 A * | 9/2012 | ............. H04N 5/775 |
| JP | 2013-034764 A | 2/2013 | |
| WO | 2008-026258 A1 | 3/2008 | |

OTHER PUBLICATIONS

Azuma, "A Survey of Augmented Reality," Presence, 1997, vol. 6, No. 4, pp. 355-385.

Vogt et al., "Reality Augmentation for Medical Procedures: System Architecture, Single Camera Marker Tracking, and System Evaluation," International Journal of Computer Vision, 2006, vol. 70, No. 2, pp. 179-190.

Navab et al., Action- and Workflow-Driven Augmented Reality for Computer-Aided Medical Procedures, IEEE Computer and Graphics Applications, Projects in VR, Sep./Oct. 2007, vol. 27, No. 5, pp. 10-14.

Padoy et al., "On-line Recognition of Surgical Activity for Monitoring in the Operating Room," Proceeding of the 20th Conference on Innovative Applications of Artificial Intelligence, Jul. 1, 2008, pp. 1718-1724.

Apr. 28, 2015 International Search Report issued in International Patent Application No. PCT/JP2014/003697.

Apr. 28, 2015 Written Opinion issued in International Patent Application No. PCT/JP2014/003697.

Aug. 7, 2017 Office Action issued in U.S. Appl. No. 14/901,198.

Nov. 27, 2017 Office Action issued in U.S. Appl. No. 14/901,198.

Jun. 21, 2019 Office Action issued in U.S. Appl. No. 16/026,214.

Oct. 17, 2019 Office Action Issued in U.S. Appl. No. 16/026,214.

Lindert, E.J. Van et al. "The use of a head-mounted display for visualization in neuroendoscopy". Computed Aided Surgery, vol. 9, No. 6, pp. 251-256, Jan. 2004.

Apr. 5, 2018 Notice of Allowance issued in U.S. Appl. No. 14/901,198.

Jan. 28, 2020 Notice of Allowance issued in U.S. Appl. No. 16/026,214.

Feb. 13, 2020 Corrected Notice of Allowability issued in U.S. Appl. No. 16/026,214.

\* cited by examiner

```
                                    ┌─ 381
NUMBER OF PIXELS :  XXX * XX
ASPECT RATIO :      XX : X
RESOLUTION :        XXXdpi
COMPRESSION METHOD : XXXXXXX

ENCODING METHOD :   XXXX

⋮
```

| | IDENTIFIER | INTER-APPARATUS RELATIONSHIP | ROLE | VIDEO SPECIFICATION |
|---|---|---|---|---|
| E01 | 1 | MASTER | OPERATING SURGEON | SPECIFICATION A |
| E02 | 2 | SLAVE | FIRST ASSISTANT | SPECIFICATION A |
| E03 | 3 | SLAVE | SECOND ASSISTANT | SPECIFICATION B |
| | ⋮ | ⋮ | ⋮ | ⋮ |
| E0n | n | SLAVE | NURSE | SPECIFICATION E |

382

| OPERATIVE METHOD | CONDITION | SYMPTOM | EMERGENCY RESPONSE |
|---|---|---|---|
| XXXXXX | BLOOD PRESSURE <XX | DECREASE IN BLOOD PRESSURE | RAPIDLY TRANSFUSE XXX BLOOD |
| XXXXXX | WEIGHT OF GAUZE >XX | HEMORRHAGE | RAPIDLY TRANSFUSE XXX BLOOD, GIVE XXX MEDICINE TO |
| ⋮ | ⋮ | ⋮ | ⋮ |

INFORMATION PROCESSING APPARATUS, INFORMATION PROCESSING METHOD, AND INFORMATION PROCESSING SYSTEM

This is a Continuation of application Ser. No. 16/026,214 filed, Jul. 3, 2018 which is allowed and claims the benefit of U.S. patent application Ser. No. 14/901,198, filed on Dec. 28, 2015, which is patented and claims priority to PCT Application No. PCT/JP2014/003697, filed on Jul. 11, 2014. The disclosure of each of the prior applications is hereby incorporated by reference herein in its entirety.

TECHNICAL FIELD

The present invention relates to an information processing apparatus.

BACKGROUND ART

There is known a head mounted display apparatus (a head mounted display (HMD)) which is a display apparatus mounted on the head. For example, the head mounted display apparatus generates image light for an image using a liquid crystal display and a light source, and leads the generated image light to the eyes of a user using a projection optical system, a light guide plate, or the like, and thus the user is allowed to recognize a virtual image.

PTL 1 discloses a system in which the head mounted display apparatus is used, which improves display of information in a medical environment. In the technology disclosed in PTL 1, information is acquired from a plurality of information sources based on a query. The acquired information undergoes a filtering process based on rules and is projected on eyepieces of a headset-type eyeglass viewer. In the technology disclosed in PTL 1, a control right and a priority right for display of the information on a fixed large display are determined based on a visual line of a person that wears the head mounted display apparatus. PTL 2 discloses a face mounted video display apparatus for medical use (a head mounted display apparatus). In the technology disclosed in PTL 2, operation state information of peripheral devices of an endoscope, which are used with the endoscope for an endoscopic examination or an endoscopic surgery, is displayed on the head mounted display apparatus. PTL 3 and PTL 4 disclose a method in which an augmented reality technology is applied to display information of a dental surgery in the head mounted display apparatus. In the technology disclosed in PTL 3 and PTL 4, display of a preoperative image, a simulated image, or the like for an operated part is superimposed on an actual image of an operated part.

CITATION LIST

Patent Literature

[PTL 1]
JP-A-2006-102495
[PTL 2]
JP-A-2001-104331
[PTL 3]
JP-A-2010-259497
[PTL 4]
JP-A-2013-34764

SUMMARY OF INVENTION

Technical Problem

Progresses in Medicine and electronic devices have brought about rapid progress in current medical locations. In the medical locations, various apparatuses for medical use (hereinafter, referred to as "medical apparatuses") such as an electrocardiogram, a heart rate meter, a blood pressure meter, a pulse oximeter, a blood glucose meter, an X-ray, and an endoscope are used. It is a great burden for those in the medical locations to understand information of the various medical apparatuses and to perform tasks. For this reason, there has been a demand for a system in which all the information of the various medical apparatuses can be unified. In the technology disclosed in PTL 1, information can be acquired from a plurality of information sources (medical apparatuses), but there is no mention of how the acquired information is displayed on a plurality of the head mounted display apparatuses. In the technologies disclosed in PTL 2 to PTL 4, targeted medical apparatuses are limited, and thus there is a problem in that the information of the various medical apparatuses cannot be unified.

The problem is not limited to the head mounted display apparatus, but is common to all information processing apparatuses that generate information to be displayed on an image display apparatus such as the head mounted display apparatus. As such, there is a demand for an information processing apparatus that can unify the information of the various medical apparatuses, and that can control a display of the information on a plurality of image display apparatuses. In addition, there are various demands for the information processing apparatus as follows: a versatility improvement, a convenience improvement, a manufacturing cost reduction, and a reliability improvement.

Solution to Problem

An advantage of some aspects of the invention is to solve at least a part of the problems described above, and the invention can be implemented as the following aspects.

(1) An aspect of the invention provides an information processing apparatus. The information processing apparatus includes an acquisition unit that acquires plural pieces of medical apparatus information which are plural pieces of information acquired from a plurality of medical apparatuses; a generation unit that generates plural pieces of presentation information which respectively contain at least a part of the plural pieces of medical apparatus information acquired by the acquisition unit; and a presentation unit that outputs the generated presentation information to a plurality of image display apparatuses. In the information processing apparatus according to the aspect, the generation unit generates the presentation information using the plural pieces of medical apparatus information acquired by the acquisition unit, and thus the information (the medical apparatus information) of various medical apparatuses which are connected to the information processing apparatus can be unified. The presentation unit outputs the generated presentation information to the plurality of image display apparatuses, and thus the generation unit can control display on the plurality of image display apparatuses. As a result, it is possible to unify the information of various medical apparatuses, and it is possible to realize the information processing apparatus that can control the display on the plurality of image display apparatuses.

(2) The information processing apparatus according to the aspect described above may be configured such that the generation unit has a first mode in which the presentation information common to the plurality of image display apparatuses is generated, and a second mode in which the plural pieces of presentation information are generated to respectively correspond to the plurality of image display apparatuses. In the information processing apparatus according to this aspect, the generation unit has the first mode in which the presentation information common to the plurality of image display apparatuses is generated using the unified medical apparatus information, and the second mode in which the plural pieces of presentation information are generated to respectively correspond to the plurality of image display apparatuses. The generation unit uses the modes separately, and thus the information processing apparatus can control the display on the plurality of image display apparatuses.

(3) The information processing apparatus according to the aspect described above may be configured such that, in the first mode, the generation unit generates the common presentation information that contains at least the medical apparatus information selected by a user of a specific image display apparatus. In the information processing apparatus according to this aspect, the generation unit generates the common presentation information that contains at least the medical apparatus information selected by the user of the specific image display apparatus, and the presentation unit outputs the generated common presentation information to the plurality of image display apparatuses. As a result, the information processing apparatus can control display on the plurality of image display apparatuses based on the selection of the user of the specific image display apparatus.

(4) The information processing apparatus according to the aspect described above may be configured such that the information processing apparatus further includes an inter-apparatus relationship storage unit that stores information for individually identifying the plurality of image display apparatuses in association with information for indicating whether the image display apparatus is the specific image display apparatus, and in the first mode, the generation unit identifies the specific image display apparatus using the inter-apparatus relationship storage unit. In the information processing apparatus according to this aspect, the generation unit can simply identify the specific image display apparatus from the plurality of image display apparatuses using the inter-apparatus relationship storage unit.

(5) The information processing apparatus according to the aspect described above may be configured such that, in the second mode, the generation unit generates the plural pieces of presentation information that respectively contain at least the pieces of acquired medical apparatus information which are respectively selected by users of the plurality of image display apparatuses. In the information processing apparatus according to this aspect, the generation unit generates the plural pieces of presentation information that respectively contain at least the pieces of medical apparatus information which are respectively selected by the users of the plurality of image display apparatuses. The presentation unit outputs the plural pieces of generated presentation information to the plurality of image display apparatuses. As a result, the information processing apparatus can individually control display on the plurality of image display apparatuses based on a selection of each user of the image display apparatus.

(6) The information processing apparatus according to the aspect described above may be configured such that, in the second mode, the generation unit generates the plural pieces of presentation information that respectively contain at least the pieces of medical apparatus information acquired from the medical apparatuses based on the role of each user. In the information processing apparatus according to this aspect, the generation unit generates the plural pieces of presentation information that respectively contain at least the pieces of medical apparatus information which are acquired from the medical apparatuses based on the role of each user. The presentation unit outputs the plural pieces of generated presentation information to the plurality of image display apparatuses. As a result, the information processing apparatus can individually control display on the plurality of image display apparatuses based on the role of each user of the image display apparatus, and it is possible to improve convenience of each user of the image display apparatus.

(7) The information processing apparatus according to the aspect described above may be configured such that the information processing apparatus further includes a role storage unit that stores the information for individually identifying the plurality of image display apparatuses in association with a role of a user of the image display apparatus, and in the second mode, the generation unit identifies the role of the user using the role storage unit. In the information processing apparatus according to this aspect, the generation unit can simply identify a role of each user using the role storage unit.

(8) The information processing apparatus according to the aspect described above may be configured such that, in the second mode, the generation unit further generates combined information in which the plural pieces of generated presentation information are combined together, and the presentation unit outputs the combined information that is generated for the specific image display apparatus. In the information processing apparatus according to this aspect, the generation unit generates the combined information in which the plural pieces of generated presentation information are combined together, and the presentation unit outputs the combined information that is generated for the specific image display apparatus. As a result, the user of the specific image display apparatus can understand what presentation information is displayed on the plurality of image display apparatuses connected to the information processing apparatus. As a result, it is possible to improve convenience of the user of the specific image display apparatus.

(9) The information processing apparatus according to the aspect described above may be configured such that, when the generation unit generates the presentation information, the generation unit enlarges or reduce an image while maintaining an aspect ratio of the image that is contained in the medical apparatus information. In the information processing apparatus according to this aspect, the generation unit enlarges or reduces the image while maintaining the aspect ratio of the image that is contained in the medical apparatus information, and thus it is possible to suppress unexpected distortion of the medical apparatus information acquired by the medical apparatus when the presentation information is generated.

(10) The information processing apparatus according to the aspect described above may be configured such that the information processing apparatus is connected to a head mounted display apparatus as the image display apparatus, on which a user can see a virtual image and an outside scene. In the information processing apparatus according to this aspect, it is possible to unify the information of various medical apparatuses, and it is possible to realize the information processing apparatus that can control display on the plurality of head mounted display apparatuses.

(11) The information processing apparatus according to the aspect described above may be configured such that the presentation unit further acquires from the head mounted display apparatus an image in a direction of a visual field of a user that wears the head mounted display apparatus, the presentation unit further extracts characteristics of an object contained in the outside scene by recognizing the image acquired in the direction of the visual field, and the presentation unit further compensates the presentation information generated by the generation unit based on the extracted characteristics, and outputs the compensated presentation information. In the information processing apparatus according to this aspect, the presentation unit extracts the characteristics of the object contained in the outer scene by recognizing the image in the direction of the visual field of the user of the head mounted display apparatus, and the presentation unit compensates the generated presentation information based on the extracted characteristics. For this reason, when the presentation information contains invisible part information such as a CT image, an MRI image, or an X-ray image, it is possible to align the invisible part information with the object (for example, the body of a patient) contained in the outside scene. As a result, it is possible to improve convenience of the user of the head mounted display apparatus. Furthermore, since the head mounted display apparatus can receive the compensated presentation information, the head mounted display apparatus may display the received presentation information as it is. As a result, it is possible to simplify a configuration of the head mounted display apparatus.

(12) The information processing apparatus according to the aspect described above may be configured such that the information processing apparatus further includes a step management unit that transmits information on a predetermined step to the generation unit, and that changes the step to be transmitted based on the plural pieces of medical apparatus information acquired by the acquisition unit, and the generation unit generates the presentation information that contains the received step. In the information processing apparatus according to this aspect, the step management unit transmits the information on the predetermined step to the generation unit, and the generation unit generates the presentation information that contains the received step. For this reason, the information processing apparatus can display the predetermined step on the plurality of image display apparatuses connected to the information processing apparatus. The step management unit changes the step to be transmitted based on the plural pieces of medical apparatus information that are acquired by the acquisition unit. For this reason, the information processing apparatus can change the step to be displayed on the plurality of image display apparatuses based on the plural pieces of medical apparatus information that are acquired by the plurality of medical apparatuses. As a result, it is possible to provide the information processing apparatus that can flexibly change the predetermined step based on the medical apparatus information, and can guide each user of the image display apparatus through the step.

(13) The information processing apparatus according to the aspect described above may be configured such that the step management unit repeatedly acquires the plural pieces of medical apparatus information, and changes the step to be transmitted to the generation unit based on the plural pieces of latest medical apparatus information. In the information processing apparatus according to this aspect, the step management unit repeatedly acquires the plural pieces of medical apparatus information, and changes the step to be transmitted to the generation unit based on the plural pieces of latest medical apparatus information. For this reason, the information processing apparatus can change the step to be displayed on the plurality of image display apparatuses in real time based on the plural pieces of medical apparatus information that are acquired from the plurality of medical apparatuses.

(14) The information processing apparatus according to the aspect described above may be configured such that the step management unit transmits to the generation unit information on a series of predetermined steps which are formed of a plurality of steps, and the step management unit changes the steps by performing at least one of the following procedures: addition of a new step to the series of steps, removal of at least a part of steps from the series of steps, and replacement of at least a part of steps in the series of steps. In the information processing apparatus according to this aspect, the step management unit may change the steps by performing at least one of the following procedures: addition of a new step to the series of steps, removal of at least a part of steps from the series of steps, and replacement of at least a part of steps in the series of steps.

(15) The information processing apparatus according to this aspect described above may be configured such that the step management unit sequentially transmits to the generation unit the series of predetermined steps one by one, which are formed of the plurality of steps and the step management unit changes the steps by stopping the transmission of the single step. In the information processing apparatus according to this aspect, the step management unit can change the steps by stopping the transmission of the step.

(16) The information processing apparatus according to the aspect described above may be configured such that, in the first mode, the step management unit transmits the steps for the user of the specific image display apparatus to the generation unit. In the information processing apparatus according to this aspect, in the first mode, the step management unit transmits the steps for the user of the specific image display apparatus to the generation unit. For this reason, the information processing apparatus can display common "steps for the user of the specific image display apparatus" on the plurality of image display apparatuses.

(17) The information processing apparatus according to the aspect described above may be configured such that, in the second mode, the step management unit transmits to the generation unit the steps that respectively correspond to the roles of the users. In the information processing apparatus according to this aspect, in the second mode, the step management unit transmits to the generation unit the steps that respectively correspond to the roles of the users. For this reason, the information processing apparatus can individually display the "steps which respectively correspond to the roles of the users of the image display apparatuses" on the plurality of image display apparatuses.

(18) Another aspect of the invention provides an information processing system. The information processing system includes a plurality of medical apparatuses; an information processing apparatus; and a plurality of head mounted display apparatuses, on each of which a user can see a virtual image and an outside scene. The information processing apparatus includes an acquisition unit that acquires plural pieces of medical apparatus information that are acquired from the plurality of medical apparatuses; a generation unit that generates presentation information which contains at least a part of the plural pieces of medical apparatus information acquired by the acquisition unit; and a presentation unit that outputs the generated presentation information to the plurality of head mounted display apparatuses. The head mounted display apparatus includes a presentation information acquisition unit that acquires the presentation information from the information processing apparatus; and an image display unit on which a user of the head mounted display apparatus sees the acquired presentation information as the virtual image. In the information processing system according to the aspect, it is possible to unify information of various medical apparatus (medical apparatus information) using the information processing apparatus, and it is possible to realize the information processing system in which display on the plurality of head mounted display apparatuses can be controlled.

Not the entirety of a plurality of configuration elements of each aspect of the invention is essential. It is possible to appropriately change, remove, replace a part of the plurality of configuration elements with new configuration elements, or to remove a part of limited content so as to solve a part or the entirety of the problems, or to achieve a part or the entirety of the advantages described in this specification. A part or the entirety of technical characteristics contained in one aspect of the invention can be combined with a part or the entirety of technical characteristics contained in the other aspects of the invention, or can be an independent aspect of the invention so as to solve a part or the entirety of the problems, or to achieve a part or the entirety of the advantages described in this specification.

For example, an aspect of the invention can be realized as an apparatus that includes a part or the entirety of three configuration elements which are the acquisition unit, the generation unit, and the presentation unit. That is, the apparatus may or may not include the acquisition unit. The apparatus may or may not include the generation unit. The apparatus may or may not include the presentation unit. For example, the apparatus can be realized as the information processing apparatus, but the apparatus can also be realized as apparatuses other than the information processing apparatus. A part or the entirety of the technical characteristics of each aspect of the information processing apparatus can be applied to any apparatus.

The invention can be realized in various forms. For example, it is possible to realize the invention in the following forms: the information processing apparatus; the information processing method; the information processing system; the head mounted display apparatus; a method of controlling the head mounted display apparatus; a head mounted display system; a computer program for the realization of functions of the methods, the apparatuses, and the systems, a record medium on which the computer program is recorded, and the like.

DESCRIPTION OF EMBODIMENTS

A. First Embodiment

Figure 1:
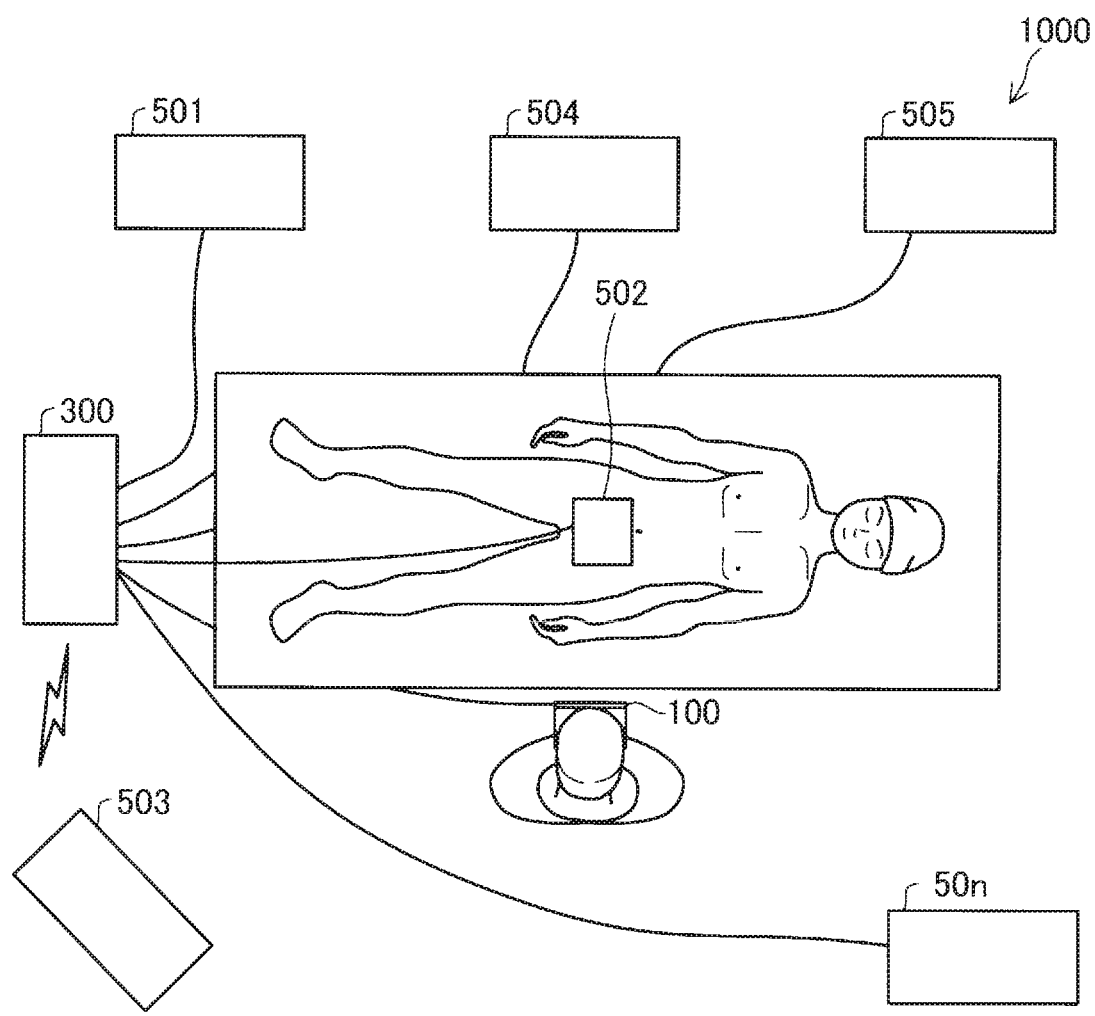
FIG. 1 is a diagram illustrating a schematic configuration of an information processing system according to an embodiment of the invention.

A-1. Configuration of Information Processing System:

FIG. 1 is a diagram illustrating a schematic configuration of an information processing system 1000 according to an embodiment of the invention. The information processing system 1000 includes a plurality of medical apparatuses 501 to 50n, an information processing apparatus 300, and an image display apparatus 100. The information processing system 1000 is a system used in a medical location. The information processing apparatus 300 acquires information from the plurality of medical apparatuses 501 to 50n, unifies the information, and generates presentation information to be displayed on the image display apparatus 100. The medical apparatuses 501 to 50n and the image display apparatus 100 are connected to the information processing apparatus 300 by a wired connection or a wireless connection. Hereinafter, "n" is used as a letter indicating an "arbitrary plural". n is an integer equal to or greater than 1.

Figure 2:
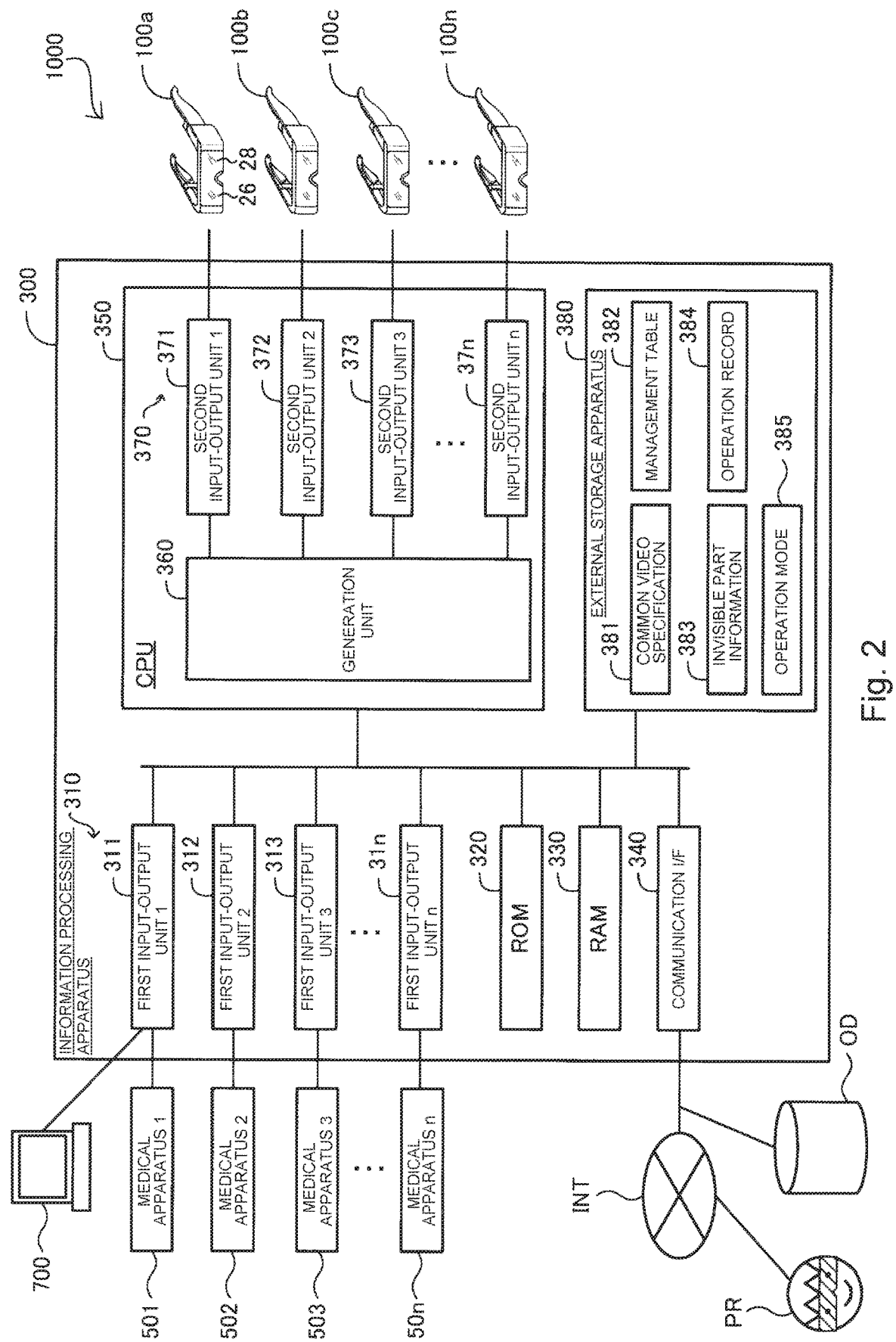
FIG. 2 is a block diagram illustrating a functional configuration of an information processing apparatus.

In the embodiment, an operation site in an operation room is illustrated as the medical location. However, the information processing system 1000 may be used in a consulting room, a treatment room, a curing room, a delivery room, and the like. In the embodiment, a head mounted display apparatus is illustrated as the image display apparatus 100. However, the image display apparatus 100 may be a stationary display, a portable display, a smart phone, and the like. Hereinafter, the head mounted display apparatus 100 is also referred to as the "head mounted display (HMD) 100". In FIG. 1, a single head mounted display 100 is illustrated. However, as illustrated in FIG. 2 to be described below, a plurality of head mounted displays 100a to 100n may be connected to the information processing apparatus 300.

In the following description, when the head mounted displays 100a to 100n are not particularly specified and are generally described, the head mounted displays 100a to 100n are simply referred to as the "head mounted display 100". Similarly, when the medical apparatuses 501 to 50n are not particularly specified and are generally described, the medical apparatuses 501 to 50n are simply referred to as a "medical apparatus 500".

The medical apparatuses 501 to 50n are various apparatuses for a medical use. For example, the following can be used as the medical apparatuses 501 to 50n: a visible light camera for photographing indoor and outdoor still images and indoor and outdoor moving images, a visible light camera for photographing still and moving images of an operated part, an electrocardiogram examination apparatus, a timer for surgery, a biological monitor, a heart rate meter, a pulse rate meter, a blood pressure meter, an ultrasonic examination apparatus, a pulse oximeter, a blood glucose meter, a CT (Computed Tomography) image photographing apparatus, an MRI (Magnetic Resonance Imaging) image photographing apparatus, an X-ray image photographing apparatus, a fluoroscopic image photographing apparatus, an endoscopic image photographing apparatus, a thermography image photographing apparatus, and the like.

A-2. Configuration of Information Processing Apparatus:

FIG. 2 is a block diagram illustrating a functional configuration of the information processing apparatus 300. The information processing apparatus 300 includes a first input/output unit 310, a ROM 320, a RAM 330, a communication interface 340, a CPU 350, and an external storage apparatus 380. The units are connected to each other via a bus.

The first input/output unit 310 as an acquisition unit includes a plurality of first input/output units 311 to 31n. For example, the first input/output units 311 to 31n are the following input/output interfaces conforming to a communication standard: a USB (Universal Serial Bus), an HDMI (High Definition Multimedia Interface), a DVI (Digital Visual Interface), a VGA (Video Graphics Array), a composite, an RS-232C (Recommended Standard 232), an infrared ray, a short-range wireless communication (for example, Bluetooth (registered trademark)), a wireless LAN (for example, IEEE802.11), a wired LAN (for example, IEEE802.3), and the like. The first input/output units 311 to 31n respectively acquire information input from the medical apparatuses 501 to 50n that are respectively connected thereto. The information input from the medical apparatus is information measured by or photographed by the medical apparatus. Hereinafter, the information is also referred to as "medical apparatus information".

In the embodiment, the first input/output unit 311 is an input/output interface conforming to the DVI. The first input/output unit 312 is an input/output interface conforming to the HDMI. The first input/output unit 313 is an input/output interface conforming to the HDMI. The first input/output unit 31n is an input/output interface conforming to the wireless LAN. In FIG. 2, the medical apparatus 501 and a stationary display 700 are connected to the first input/output unit 311. Similarly, the medical apparatus 502 is connected to the first input/output unit 312, the medical apparatus 503 is connected to the first input/output unit 313, and the medical apparatus 50n is connected to the first input/output unit 31n. In this way, the first input/output unit 310 is configured to have the first input/output units 311 to 31n conforming to the different types of communication standards. For this reason, it is possible to connect the medical apparatuses conforming to various communication standards and the first input/output unit 310, and it is possible to improve versatility of the information processing apparatus 300. The first input/output unit 310 can also output to the display apparatus such as the display 700 an input signal as it is.

The communication interface (I/F) 340 is a wired LAN interface. The communication interface 340 communicatively connects a doctor PR in an external facility and the information processing apparatus 300 via an Internet INT line. The communication interface 340 communicatively connects a database OD connected to an in-hospital LAN and the information processing apparatus 300 via an intranet. For example, the doctor PR is assumed to be a doctor who supervises a user of the head mounted display 100 that is connected to the information processing apparatus 300, or is assumed to be an outside expert. The database OD stores procedure information illustrating a procedure of a treatment such as an operation, an electronic medical record system, electronic academic books, and the like.

The CPU 350 deploys and executes a computer program stored in the ROM 320 on the RAM 330 to thereby control the information processing apparatus 300. The CPU 350 realizes each function of a generation unit 360 and a second input/output unit 370. The generation unit 360 generates presentation information to be displayed on the head mounted display 100 by executing a presentation information generating process to be described below. The generation unit 360 of the embodiment has the following two modes as processing modes in the presentation information generating process.

(1) First mode in which common presentation information is generated (2) Second mode in which plural pieces of presentation information are generated to respectively correspond to the head mounted displays 100a to 100n The second input/output unit 370 as a presentation unit includes a plurality of second input/output units 371 to 37n. Similarly to the first input/output unit 310, the second input/output units 371 to 37n are input/output interfaces conforming to various communication standards. Since the detail is the same as that of the first input/output unit 310, the descriptions thereof will be omitted.

In the embodiment, the second input/output unit 371 and the second input/output unit 372 are input/output interfaces conforming to the wireless LAN. The second input/output unit 373 is an input/output interface conforming to the USB. The second input/output unit 37n is an input/output interface conforming to the DVI. In FIG. 2, the head mounted display 100a as the image display apparatus is connected to the second input/output unit 371. Similarly, the head mounted display 100b is connected to the second input/output unit 372, the head mounted display 100c is connected to the second input/output unit 373, and the head mounted display 100n is connected to the second input/output unit 37n. In this way, the second input/output unit 370 is configured to have the second input/output units 371 to 37n conforming to the different types of communication standards. For this reason, it is possible to connect the head mounted displays conforming to various communication standards and the second input/output unit 370, and it is possible to improve the versatility of the information processing apparatus 300.

The external storage apparatus 380 is configured to have a ROM, a RAM, a DRAM, a hard disk, a flash memory, and the like which are not illustrated. The external storage apparatus 380 stores a common video specification 381, a management table 382, invisible part information 383 as an invisible part information storage unit, an operation record 384, and an operation mode 385.

Figures 3, 4:
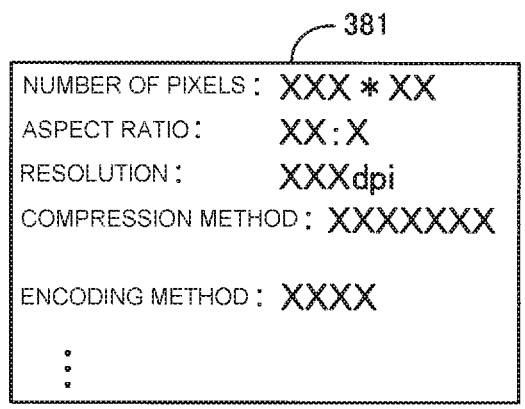
FIG. 3 is a table illustrating an example of a common video specification.
FIG. 4 is a table illustrating an example of a management table.

FIG. 3 is a table illustrating an example of the common video specification 381. The common video specification 381 is a table that defines a standard specification concerning a video signal of the presentation information. The common video specification 381 is used when the generation unit 360 generates the presentation information in the presentation information generating process.

The common video specification 381 of the embodiment includes the number of pixels, an aspect ratio, and a resolution of an image contained in the video signal, an image compression method, and an image encoding method as the specification of the video signal. The common video specification 381 is determined in advance, and is stored in the external storage apparatus 380. When the common video specification 381 is determined, the video signal specifications, which are adopted by the head mounted displays 100a to 100n connected to the second input/output unit 370, are preferably taken into consideration.

FIG. 4 is a table illustrating an example of the management table 382. The management table 382 as a role storage unit and an inter-apparatus relationship storage unit is a table for managing the information of the head mounted display 100 connected to the second input/output unit 370, more specifically, for managing the information of the head mounted displays 100a to 100n that are respectively connected to the second input/output units 371 to 37n. The management table 382 is used when the generation unit 360 generates the presentation information in the presentation information generating process, and is also used when the second input/output units 371 to 37n transmit the presentation information to the head mounted displays 100a to 100n, respectively.

An identifier, an inter-apparatus relationship, a role, and the video specification are stored in the management table 382 of the embodiment in association with each other. The "identifier" stores each unique identifier for individually identifying the head mounted displays 100 connected to the second input/output units 370. The "inter-apparatus relationship" stores a string of letters indicating master/slave relationships between the plurality of head mounted displays 100a to 100n which are connected to the second input/output units 370. In the embodiment, one head mounted display 100 is set to be a master, and the other head mounted displays 100 are set to be slaves. The "role" stores a string of letters indicating a role that the user of the head mounted display 100 identified by the identifier takes in a medical location. The "video specification" stores a string of letters indicating a pattern of the specifications (the number of pixels, the aspect ratio, the resolution of the image contained in the video signal, the image compression method, the image encoding method, and the like) of the video signal in the head mounted display 100 that is identified by the identifier.

In the example illustrated in FIG. 4, the user of the head mounted display 100 identified by an identifier "1" is an "operating surgeon", and the video specification of the head mounted display 100 is a "specification A" (an entry E01). Similarly, the user of the head mounted display 100 identified by an identifier "n" is a "nurse" and the video specification of the head mounted display 100 is a "specification E" (an entry E0n). In the example illustrated in FIG. 4, the head mounted display 100 identified by the identifier "1" is a master, and the head mounted displays 100 identified by the other identifiers are slaves (entries E01 to E0n).

The management table 382 may be determined in advance and be stored in the external storage apparatus 380. Alternatively, the management table 382 may be automatically generated in an initial process when the head mounted display 100 is connected to the information processing apparatus 300. Specifically, for example, when the generation unit 360 detects the connection of the head mounted display 100 and the second input/output unit 370, the generation unit 360 gives a unique identifier to the head mounted display 100, and acquires a designation of master/slave, a role of the user, and a video specification from the head mounted display 100. The generation unit 360 stores the given identifier, the designation of master/slave, the acquired role, and the acquired video specification in the management table 382. The initial process is performed whenever the head mounted displays 100a to 100n are respectively connected to the second input/output units 370, and thus the generation unit 360 can automatically generate the management table 382.

As described above, the "inter-apparatus relationship" in the management table 382 is acquired from the head mounted display 100. In addition, for example, the "inter-apparatus relationship" may be determined by the following methods.

The "inter-apparatus relationship" is determined based on the role that is acquired from the head mounted display 100. For example, the generation unit 360 sets the head mounted display 100 of the operating surgeon to a master, and sets the head mounted displays 100 of users other than the operating surgeon to slaves.

The "inter-apparatus relationship" is determined based on acquisition of current position information of the head mounted display 100 and a positional relationship between the head mounted displays. For example, the generation unit 360 acquires the current position information of the head mounted display 100. The generation unit 360 sets the head mounted display 100 positioned closest to a center of an operating table to a master, and sets other head mounted displays 100 to slaves.

The "inter-apparatus relationship" is determined based on differences of hardware and software configurations of the head mounted display 100. For example, the generation unit 360 acquires a model number of the head mounted display 100. The generation unit 360 sets the head mounted display 100 with a specific model number to a master, and sets other head mounted displays 100 to slaves.

As described above, the "role" in the management table 382 is acquired from the head mounted display 100. In addition, for example, the "role" may be determined by the following methods.

The "role" is determined based on current position information of the head mounted display 100. For example, the external storage apparatus 380 of the information processing apparatus 300 pre-stores layout information that contains layout of equipment (the operating table and the medical apparatus 500) in the operation room, and layout of standing positions of staffs based on the roles in the operation room. The generation unit 360 acquires the current position information of the head mounted display 100, and compares the acquired current position information with the layout information, and thus the role of the user of the head mounted display 100 is determined.

The "role" is determined based on an image (an outside scene image) in a direction of a visual field of the user of the head mounted display 100. The generation unit 360 acquires an outside scene image from the head mounted display 100, and recognizes the outside scene image. Accordingly, the generation unit 360 specifies the type of the medical apparatus 500, the type of the equipment in the operation room, a part of the patient body, and the like which the user sees. The generation unit 360 determines the role of the user of the head mounted display 100 based on the specified information.

The invisible part information 383 (the invisible part information storage unit) illustrated in FIG. 2 stores invisible part information that does not appear in an external appearance of an object. The invisible part information is image information or letter information illustrating a structure of the object. When the object is a living body, the invisible part information is, for example, a CT image, an MRI image, an X-ray image, a fluoroscopic image, an ultrasonic diagnosis image, an endoscopic image, or a thermographic image, and letter information incident to the image. The invisible part information is photographed in advance, and is stored in the invisible part information 383.

The operation record 384 illustrated in FIG. 2 is a recording unit that records the medical apparatus information acquired by the information processing apparatus 300 and the presentation information generated by the information processing apparatus 300 in association with a date and time when the information is acquired or generated. The medical apparatus information acquired by the information processing apparatus 300 indicates the medical apparatus information that the information processing apparatus 300 acquires from the plurality of medical apparatuses 501 to 50n which are respectively connected to the first input/output units 311 to 31n. The presentation information generated by the information processing apparatus 300 indicates the entire presentation information that the generation unit 360 generates in the presentation information generating process. The record of the information acquired and generated by the information processing apparatus 300 can be regarded to be the substantially same as a log of an operation (a diagnosis, a treatment, or a curing). Accordingly, in this manner, after the operation or the like is ended, it is possible to use the log of the operation in the analysis of content of the operation, training and academic purpose, and the like.

The operation mode 385 illustrated in FIG. 2 stores a processing mode (that is, an operation mode of the generation unit 360) in the presentation information generating process of the generation unit 360. Content of the operation mode 385 can be changed by an input device which the information processing apparatus 300 includes and which is not illustrated. The content of the operation mode 385 can be also changed by a change instruction from the head mounted display 100.

Figure 5:
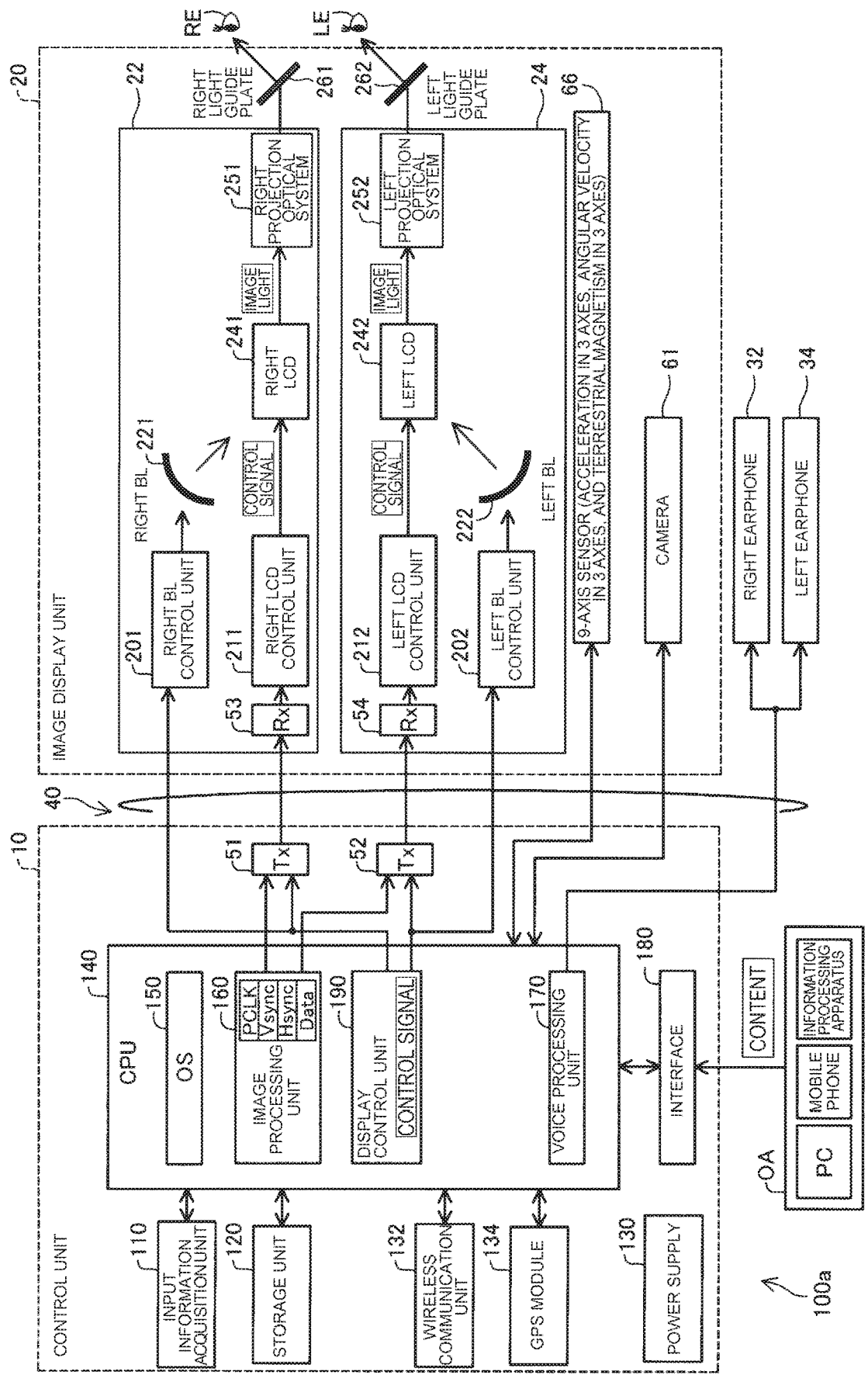
FIG. 5 is a block diagram illustrating a functional configuration of a head mounted display.

A-3. Configuration of Head Mounted Display Apparatus:

FIG. 5 is a block diagram illustrating a functional configuration of the head mounted display 100a. Hereinafter, the head mounted display 100a is illustrated and described as an example of a configuration of the head mounted display 100. The head mounted display 100a is an optical transmission type head mounted display apparatus on which a user can see a virtual image and concurrently, can directly see an outside scene. The presentation information acquired from the information processing apparatus 300 is displayed as a virtual image on the head mounted display 100a. The head mounted display 100a includes an image display unit 20 on which the user sees the virtual image in a state where the user wears the head mounted display 100a on the head, and a control unit 10 that controls the image display unit 20. Various signals are transmitted between the image display unit 20 and the control unit 10 via a cable 40.

A-3-1. Configuration of Control Unit:

The control unit 10 includes the following units: an input information acquisition unit 110 that acquires an operation input to an input device such as a touch pad, a cross key, a foot switch, a gesture, or a microphone; a storage unit 120 configured to have a ROM, a hard disk, and the like; a power supply 130 that supplies an electrical power to each unit of the head mounted display 100a; a wireless communication unit 132 that wirelessly communicates with other devices conforming to a predetermined wireless communication standard such as the wireless LAN, Bluetooth, or the like; a current position acquisition unit 134; a CPU 140; an interface 180 that connects the information processing apparatus 300 and various external devices OA; and transmitting units (Tx) 51 and 52. The units are connected to each other via a bus which is not illustrated. The current position acquisition unit 134 detects a current position of the user of the head mounted display 100a by receiving a signal from a GPS satellite, and generates current position information indicating the current position of the user. The current position acquisition unit 134 may generate the current position information by receiving radio waves from a plurality of base stations and by determining strength of the received radio waves. For example, the current position information can be realized by a coordinate indicating a latitude/longitude. Similar to the first input/output unit 310 of the information processing apparatus 300, the interface 180 can conform to various communication standards.

The CPU 140 reads out and executes a computer program stored in the storage unit 120, and thus functions as the following units: an operating system (OS) 150; an image processing unit 160; a voice processing unit 170 that supplies voice signals to speakers of a right earphone 32 and a left earphone 34; and a display control unit 190. The image processing unit 160 generates a signal based on a video signal of the presentation information that is input via the interface 180 as the presentation information acquisition unit or the wireless communication unit 132. The image processing unit 160 supplies the generated signal to the image display unit 20 via the transmitting units 51 and 52 and the cable 40, and thus controls the display on the image display unit 20. The signal supplied to the image display unit 20 can be a analog signal or a digital signal which are widely known. The display control unit 190 generates a control signal to control a right display driving unit 22 and a left display driving unit 24 of the image display unit 20, and the control signal is transmitted via the transmitting units 51 and 52. The control signal is an individual signal through which a right LCD control unit 211 turns on or off the driving of a right LCD 241, through which a right backlight control unit 201 turns on or off the driving of a right backlight 221, through which a left LCD control unit 212 turns on or off the driving of a left LCD 242, and through which a left backlight control unit 202 turns on or off the driving of a left backlight 222.

A-3-2. Configuration of Image Display Unit:

The image display unit 20 is a mounting body that the user wears on the head. In the embodiment, the image display unit 20 has an eyeglass shape. The image display unit 20 includes the right display driving unit 22 and the left display driving unit 24 that generate and emit image light for an image; a right optical image display unit 26 and a left optical image display unit 28 (refer to FIG. 2) that guide the image light to both eyes of the user; a camera 61 as the image acquisition unit, and a 9-axis sensor 66.

The right display driving unit 22 includes a receiving unit (Rx) 53; the right backlight (BL) control unit 201 and the right backlight (BL) 221 which function as light sources; the right LCD (Liquid Crystal Display) control unit 211 and the right LCD 241 which function as a display element; and a right projection optical system 251. The right backlight control unit 201 drives the right backlight 221 based on a control signal that is input via the receiving unit 53. The right backlight 221 is a light emitting body such as an LED or an electroluminescence (EL). The right LCD control unit 211 drives the right LCD 241 based on an input video signal. The right LCD 241 is a transmissive liquid crystal panel on which a plurality of pixels are arranged in a matrix shape. The right LCD 241 drives liquid crystal at a position of each of the pixels that are arranged in a matrix shape. Accordingly, the right LCD 241 changes transmittance of light that transmits through the right LCD 241, and modulates illumination light irradiated from the right backlight 221 to effective image light for the image. The right projection optical system 251 is configured to have a collimate lens that converts the image light emitted from the right LCD 241 into parallel light fluxes. The left display driving unit 24 has the same configuration as that of the right display driving unit 22 and operates similar to the right display driving unit 22.

The right optical image display unit 26 and the left optical image display unit 28 are arranged to be positioned in front of the right and left eyes of the user when the user wears the image display unit 20 (refer to FIG. 2). The right optical image display unit 26 includes a right light guide plate 261 formed of a light transmissive resin material or the like. The right light guide plate 261 reflects the image light along a predetermined optical path to guide the image light output from the right display driving unit 22 to a right eye RE of the user. A diffraction grating or a semi-transmissive reflective film may be used in the right light guide plate 261. The left optical image display unit 28 has the same configuration as that of the right optical image display unit 26, and operates similar to the right optical image display unit 26. In this way, the image light guided to both eyes of the user of the head mounted display 100a is focused on the retinas of the user, and thus the user can see the virtual image. The user of the head mounted display 100a of the embodiment can concurrently see the virtual image and the outside scene in the background of the virtual image in a portion of the visual field where the virtual image is displayed. In a portion of the visual field where the virtual image is not displayed, the user can directly see the outside scene through the right optical image display unit 26 and the left optical image display unit 28.

The 9-axis sensor 66 is a motion sensor that detects acceleration (3 axes), angular velocities (3 axes), and terrestrial magnetism (3 axes). When the user wears the image display unit 20 on the head, the 9-axis sensor 66 functions as a movement detecting unit that detects a movement of the head of the user of the head mounted display 100a. Here, the movement of the head includes changes in velocity, acceleration, angular velocity, direction, and orientation of the head. The orientation of the head is also referred to as "orientation information". The camera 61 as a visual field image acquisition unit is arranged at a position that corresponds to the middle of the forehead of the user when the user wears the image display unit 20. The camera 61 photographs an image of the outside scene in a front direction of the image display unit 20, in other words, in the direction of the visual field of the user in a state where the user wears the head mounted display 100a, and the camera 61 acquires the outside scene image. The camera 61 is a so-called visible light camera. The camera 61 of the embodiment is a monocular camera, but a stereo camera may be adopted.

Figure 6:
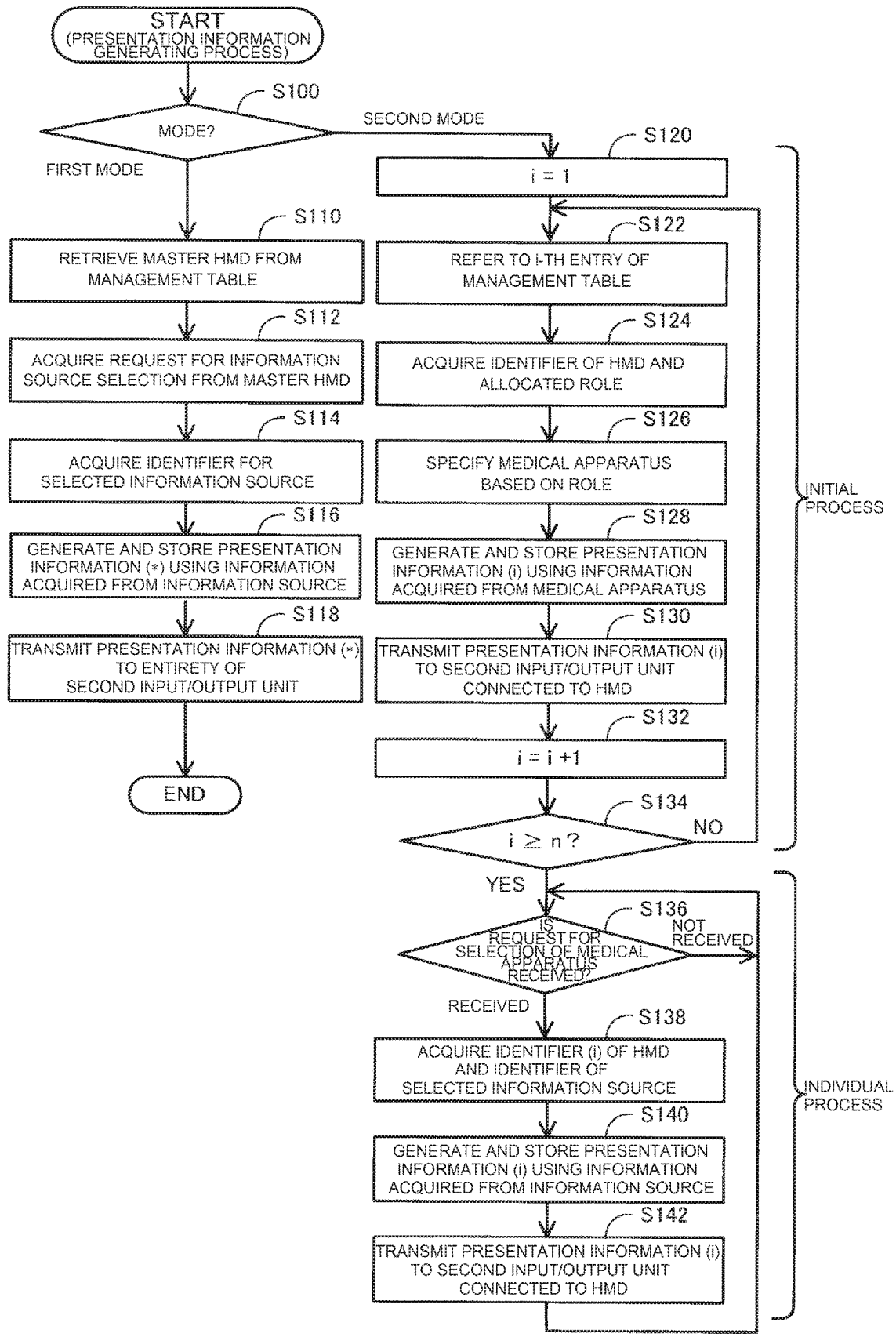
FIG. 6 is a flow chart illustrating procedures of presentation information generating process.

A-4. Presentation Information Generating Process:

FIG. 6 is a flow chart illustrating procedures of the presentation information generating process. The presentation information generating process is a process of generating the presentation information to be displayed on the head mounted display 100, and is executed by the generation unit 360 of the information processing apparatus 300 (refer to FIG. 2). The presentation information generating process is divided into the first mode in which the common presentation information is generated, and the second mode in which the plural pieces of presentation information are generated to respectively correspond to the head mounted displays 100a to 100n. The process executed in the second mode can be roughly divided into an initial process of steps S120 to S134 and an individual process of steps S136 to S142.

The generation unit 360 confirms an operation mode of the generation unit 360 with reference to content that is stored in the operation mode 385 (step S100).

A-4-1. First Mode:

When the operation mode is the "first mode" (step S100: the first mode), the generation unit 360 retrieves the master head mounted display 100 from the management table 382 (step S110). Specifically, the generation unit 360 retrieves an entry, the "inter-apparatus relationship" of which is stored as a master, with reference to the management table 382, and the generation unit 360 acquires an "identifier" of the retrieved entry.

The generation unit 360 acquires a request for an information source selection from the master head mounted display 100 (step S112). Specifically, the generation unit 360 requests the head mounted display 100 with the identifier acquired in step S110 to transmit an request for the information source selection. Here, for example, the request for an information source selection indicates any one of requests listed in the following a1 to a6.

(a1) A request for reading the medical apparatus information acquired by the medical apparatus 500

(a2) A request for placing a telephone call to the doctor PR in the external facility (a3) A request for reading data recorded in the in-hospital database OD (a4) A request for reading data recorded in the invisible part information 383

(a5) A request for reading data recorded in the operation record 384

(a6) A request for reading the medical apparatus information of the medical apparatus 500, the display unit of which the user of the head mounted display 100 can hardly see The information source in the request a1 is the medical apparatus 500. Similarly, the information source in the request a2 is the doctor PR; the information source in the request a3 is the database OD; the information source in the request a4 is the invisible part information 383; the information source in the request a5 is the operation record 384; and the information source in the request a6 is the medical apparatus 500, the display unit of which the user can hardly see. Here, for example, "the medical apparatus 500, the display unit of which the user can hardly see" is a general term of the following medical apparatus 500.

The medical apparatus 500, the display unit (a display or the like) of which the user cannot see or can hardly see because the medical apparatus 500 is present at a blind spot of the user.

The medical apparatus 500, the display unit of which the user cannot see or can hardly see because the medical apparatus 500 is present in a place remote from the user.

The medical apparatus 500, the display unit of which the user cannot see or can hardly see because the medical apparatus 500 is not present at a blind spot of the user and is present in a place close to the user, but a visual line of the user faces the display unit.

The requests a1 to a6 may be individually issued, and may be combined together. However, in the embodiment, a request for information source acquisition includes at least the request a1. The request for an information source selection is appropriately issued based on an operation of the user of the head mounted display 100.

The head mounted display 100 can transmit the request for an information source selection to the information processing apparatus 300, for example, as per the following procedures b1 to b5.

(b1) The user of the head mounted display 100 inputs a desired information source and information for specifying information in the information source via the input device (a touch pad, a cross key, a foot switch, a gesture, a microphone, or the like) of the head mounted display 100. If a voice input via the microphone is adopted as an input method, it is possible to considerably improve convenience of the user when it is difficult for the user to operate the head mounted display 100 by the hands in a medical location. In the requests a1 and a6, it is not necessary to input the "information for specifying information in the information source".

(b2) The input information acquisition unit 110 of the head mounted display 100 acquires a signal based on an operation input of the user and transmits the signal to the OS 150.

(b3) The OS 150 of the head mounted display 100 generates a request for an information source selection. Specifically, in the request a1, the OS 150 generates the request for an information source selection, which includes an identifier of the head mounted display 100 and an identifier for specifying the information source designated in the procedure b1. In the requests a2 to a5, the OS 150 generates a request for an information source selection, which includes the identifier of the head mounted display 100, the identifier for specifying the information source designated in the procedure b1, and the information for specifying the information in the information source. In the request a6, the OS 150 generates a request for an information source selection which includes the identifier of the head mounted display 100, and current position information and orientation information of the head mounted display 100. The current position information and the orientation information are used to specify "the medical apparatus 500, the display unit of which the user can hardly see" in the request a6.

(b4) The OS 150 of the head mounted display 100 transmits the request for an information source selection generated in the procedure b3 to the information processing apparatus 300 to which the OS 150 is connected via the interface 180 and the wireless communication unit 132.

(b5) The second input/output unit 370 of the information processing apparatus 300 transmits the received request for an information source selection to the generation unit 360.

The generation unit 360 acquires the information for specifying the information source and the information for specifying the information in the information source, which are contained in the request for an information source selection in step S114 of in the presentation information generating process (refer to FIG. 6). Furthermore, when the current position information and the orientation information are inserted as the information for specifying the information source, the generation unit 360 compares the current position information and the orientation information with position information acquired from the entirety of other medical apparatuses 500, and the generation unit 360 specifies "the medical apparatus 500, the display unit of which the user can hardly see". In addition, in step S114, the generation unit 360 may specify "the medical apparatus 500, the display unit of which the user can hardly see" by combining the current position information and the orientation information with a movement (changes in velocity, acceleration, angular velocity, direction, and orientation) of the head of the user that is obtained by the 9-axis sensor 66 of the head mounted display 100.

The generation unit 360 accesses the designated (specified) information source to acquire the designated information. The generation unit 360 generates the common presentation information supplied to the entirety of the head mounted displays 100 connected to the second input/output units 370 using the acquired information. The common presentation information is referred to as "presentation information PN*". The generation unit 360 stores the generated presentation information PN* in the operation record 384 (step S116).

Figure 7A:
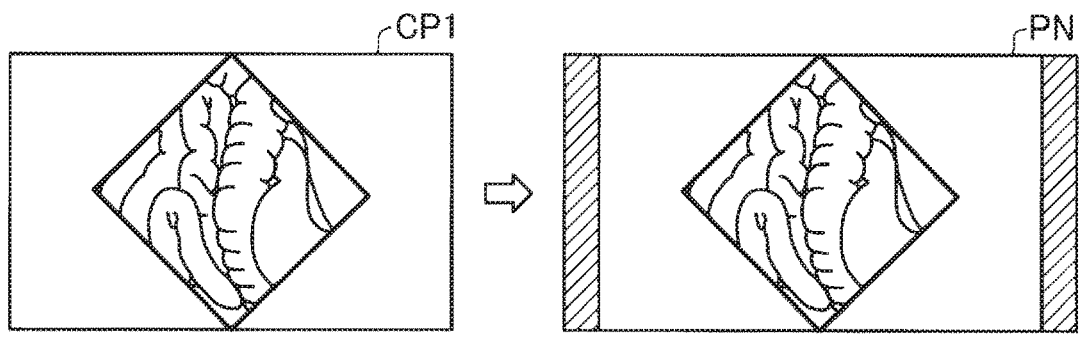
FIG. 7A illustrates a view describing a method of generating the presentation information.
Figure 7B:
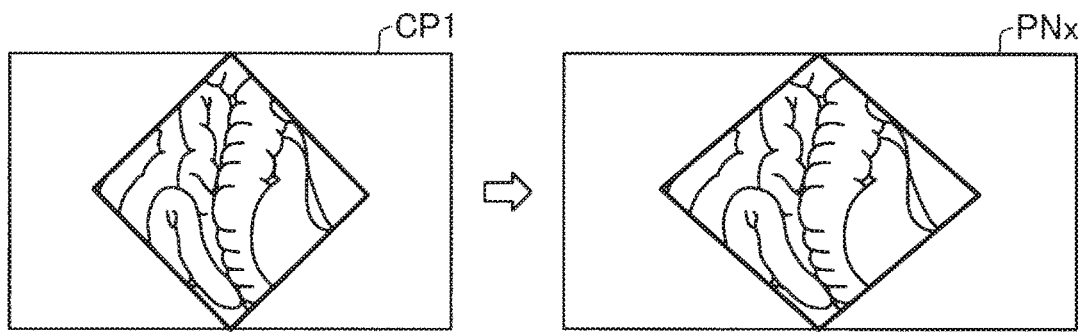
FIG. 7B illustrates a view describing a method of generating the presentation information.

FIGS. 7A and 7B illustrate views describing a method of generating the presentation information. When single information is acquired in step S116, the generation unit 360 generates presentation information PN by converting an image contained in acquired information CP1 as per the video signal specification defined in the common video specification 381 (refer to FIG. 7A). In particular, when an aspect ratio of an image contained in the acquired information CP1 is different from the aspect ratio of an image defined in the common video specification 381 during the conversion, the generation unit 360 enlarges or reduces the image while maintaining the aspect ratio of an image contained in the acquired information CP1. Then, a margin (indicated by a hatched line in FIG. 7A) is formed in a longitudinal direction or a lateral direction of the presentation information PN.

The generation unit 360 executes any one of the following procedures c1 and c2 with respect to the margin. Accordingly, the margin is displayed as a virtual image on the head mounted display 100, and thus it is possible to suppress the blockage of the visual field of the user.

(c1) The generation unit 360 inserts black dummy dot data in the margin of the presentation information PN.

(c2) The generation unit 360 sets a signal (an enable signal) to a Lo value (an invalid value) with respect the margin of the presentation information PN, and the signal is intended to perform the switching between validity and invalidity of generation of image light in the right display driving unit 22 and the left display driving unit 24 of the head mounted display 100.

In this manner, the aspect ratio of an image contained in the presentation information PN does not change. It is preferable to strictly maintain an aspect ratio of an image photographed by the medical apparatus 500 in such a manner that the user see an actual unspoiled size of the image (for example, a still image and a moving image, a CT image, an MRI image, or an X-ray image of an operated part) in a medical location where the information processing apparatus 300 is used. In this regard, if the aspect ratio of an image which is contained in the medical apparatus information CP1 acquired in step S116 is maintained, and the information source is the medical apparatus 500, it is possible to suppress unexpected distortion of the medical apparatus information measured or photographed by the medical apparatus 500. FIG. 7B illustrates presentation information PNx that is distorted because the aspect ratio of an image contained in the acquired information CP1 is not maintained, and the image is enlarged to the aspect ratio of an image defined in the common video specification 381.

Figure 8:
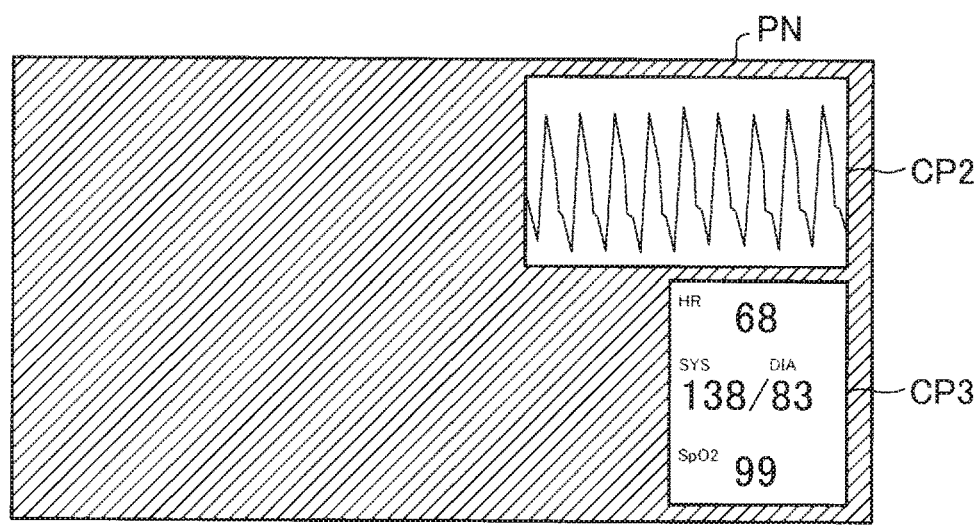
FIG. 8 is a view describing the method of generating the presentation information.

FIG. 8 is a view describing the method of generating the presentation information. When plural pieces of information are acquired in step S116, the generation unit 360 generates a first image in which the image contained in the acquired entire information (in examples illustrated in FIGS. 10A and 10B, medical apparatus information CP2 and CP3) is arranged. At this time, the generation unit 360 maintains the aspect ratio of an image contained in the acquired information. The image contained in the acquired information is preferably arranged in an end portion of the first image. The generation unit 360 generates the presentation information PN by converting the generated first image as per the video signal specification defined in the common video specification 381 (refer to FIG. 8). The generation unit 360 executes any procedure of the methods c1 and c2 with respect to a margin (indicated by a hatched line in FIG. 8) in which the image is not arranged, in the first image. Accordingly, the margin is displayed as a virtual image on the head mounted display 100, and it is possible to suppress the blockage of the visual field of the user.

Figure 9A:
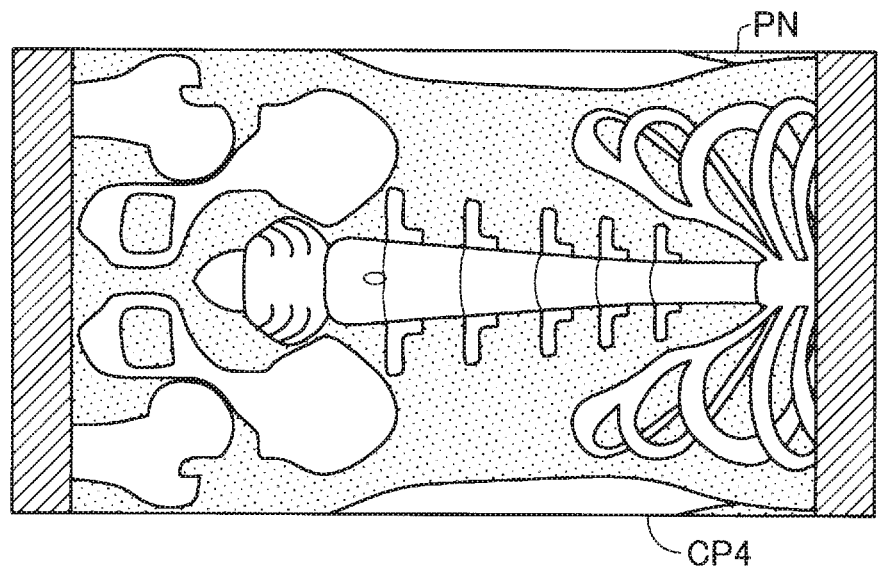
FIG. 9A illustrates a view showing a first example of the presentation information.
Figure 9B:
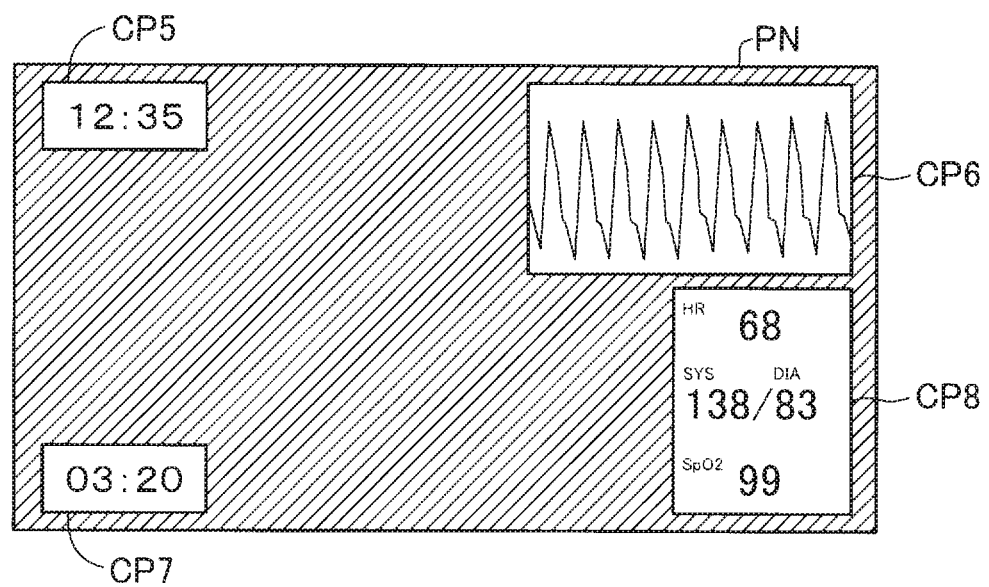
FIG. 9B illustrates a view showing a first example of the presentation information.

FIGS. 9A and 9B illustrate views showing a first example of the presentation information. FIG. 9A is an example of the presentation information PN generated by the generation unit 360 when an X-ray image (CP4) of a patient stored in the invisible part information 383 is designated in the request for an information source selection. The same presentation information as that illustrated in FIG. 9A is generated when the medical apparatus 500 (an X-ray image photographing apparatus) from which the invisible part information can be acquired is designated in the request for an information source selection.

FIG. 9B is an example of the presentation information PN generated by the generation unit 360 when a timer for surgery is designated as the medical apparatus 500, a pulse rate meter is designated as the medical apparatus 500, and a biological monitor is designated as the medical apparatus 500 in the request for an information source selection. The following is arranged in each end portion of the presentation information PN: present time CP5 acquired from the timer for surgery, time CP7 elapsed from the start of surgery, a pulse image CP6 acquired from the pulse rate meter, and an image CP8 of a heart rate (HR), a blood pressure (SYS/DIA), and arterial oxygen saturation (SpO2) acquired from the biological monitor.

Figure 10A:
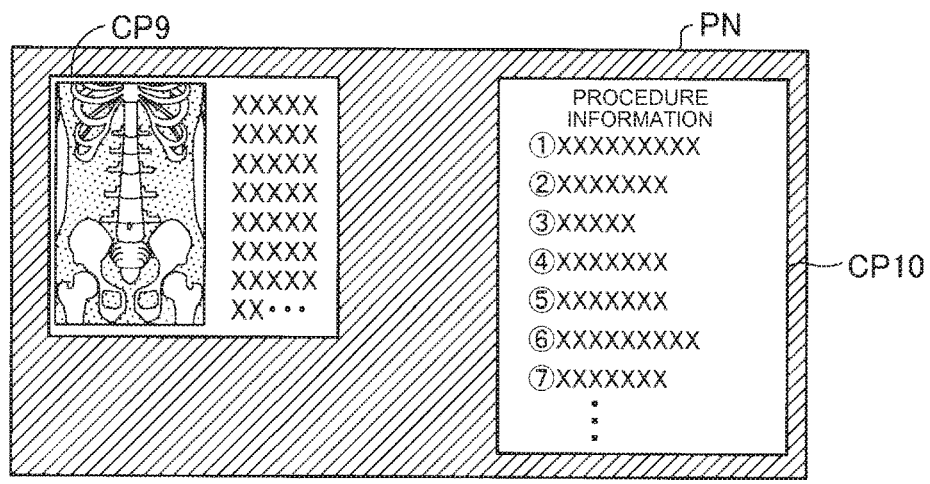
FIG. 10A illustrates a view showing a second example of the presentation information.
Figure 10B:
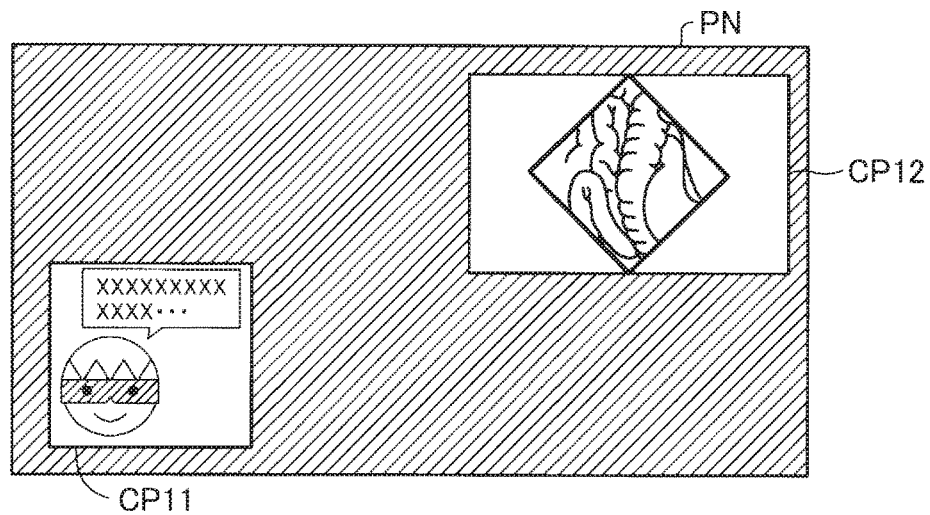
FIG. 10B illustrates a view showing a second example of the presentation information.

FIGS. 10A and 10B illustrates views showing a second example of the presentation information. FIG. 10A is an example of the presentation information PN generated by the generation unit 360 when an academic book (CP9) stored in the in-hospital database OD and operation procedure information (CP10) stored in the in-hospital database OD are designated in the request for an information source selection. FIG. 10B is an example of the presentation information PN generated by the generation unit 360 when a visible light camera for photographing a still image and a moving image of an operated part is designated as the medical apparatus 500 and a telephone call with the doctor PR in the external facility is designated in the request for an information source selection.

Figure 11:
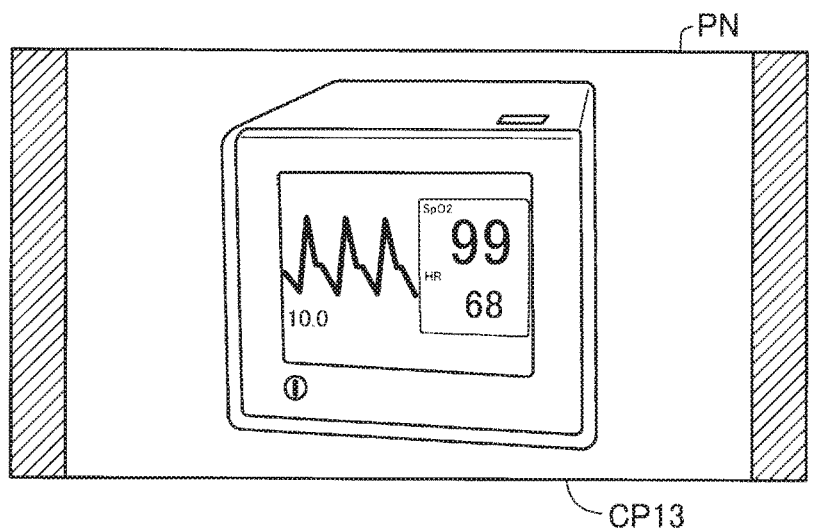
FIG. 11 is a view illustrating a third example of the presentation information.

FIG. 11 is a view illustrating a third example of the presentation information. FIG. 11 is an example of the presentation information PN generated by the generation unit 360 when the biological monitor is designated as the medical apparatus 500 in the request for an information source selection. The biological monitor illustrated in FIG. 11 does not include an interface that can be connected to the first input/output unit 310. However, when the information processing apparatus 300 is configured to include the visible light camera, and the visible light camera photographs a screen (CP13) of the biological monitor, as illustrated in FIG. 11, the generation unit 360 can generate the presentation information PN using the medical apparatus information from the medical apparatus that does not include an interface that can be connected to the first input/output unit 310.

When the presentation information PN is generated, the head mounted display 100 may directly or indirectly designate "arrangement", a "size" and "transmittance" of the information of each information source in the request for an information source selection. Here, the "direct designation" means that the head mounted display 100 designates numerical values indicating a coordinate at which each information is arranged, and a size and transmittance of each information. The "indirect designation" means that the head mounted display 100 designates a desired mode from display modes that are prepared in advance, for example, from an "outside scene priority mode" in which an outside scene is prioritized, an "image priority mode" in which an image is prioritized, and the like. For example, when the outside scene priority mode is designated, as illustrated in FIG. 8, the generation unit 360 generates the presentation information PN in such a manner that the information is arranged in a small size at an end portion of a screen so as not to interfere with the visual field of the user at the center of the screen. When the image priority mode is designated, as illustrated in FIG. 9A, the generation unit 360 generates the presentation information PN in such a manner that the information is arranged in a large size at the center of the screen.

In step S118 of the presentation information generating process (refer to FIG. 6), the generation unit 360 transmits the generated presentation information PN* to the entirety of the second input/output units 370 (the second input/output units 371 to 37n). The second input/output unit 371 converts the image contained in the received presentation information PN* as per the video signal specification of the head mounted display 100a. At this time, the second input/output unit 371 may refer to the "video specification" from the management table 382. After the conversion is performed as per the video specification, the second input/output unit 371 transmits the presentation information PN* to the head mounted display 100a. Similarly, the second input/output units 372 to 37n convert images contained in the received presentation information PN* as per the video signal specifications of the head mounted displays 100b to 100n, respectively. The second input/output units 372 to 37n transmit the converted presentation information PN* to the head mounted displays 100b to 100n, respectively.

Figure 12:
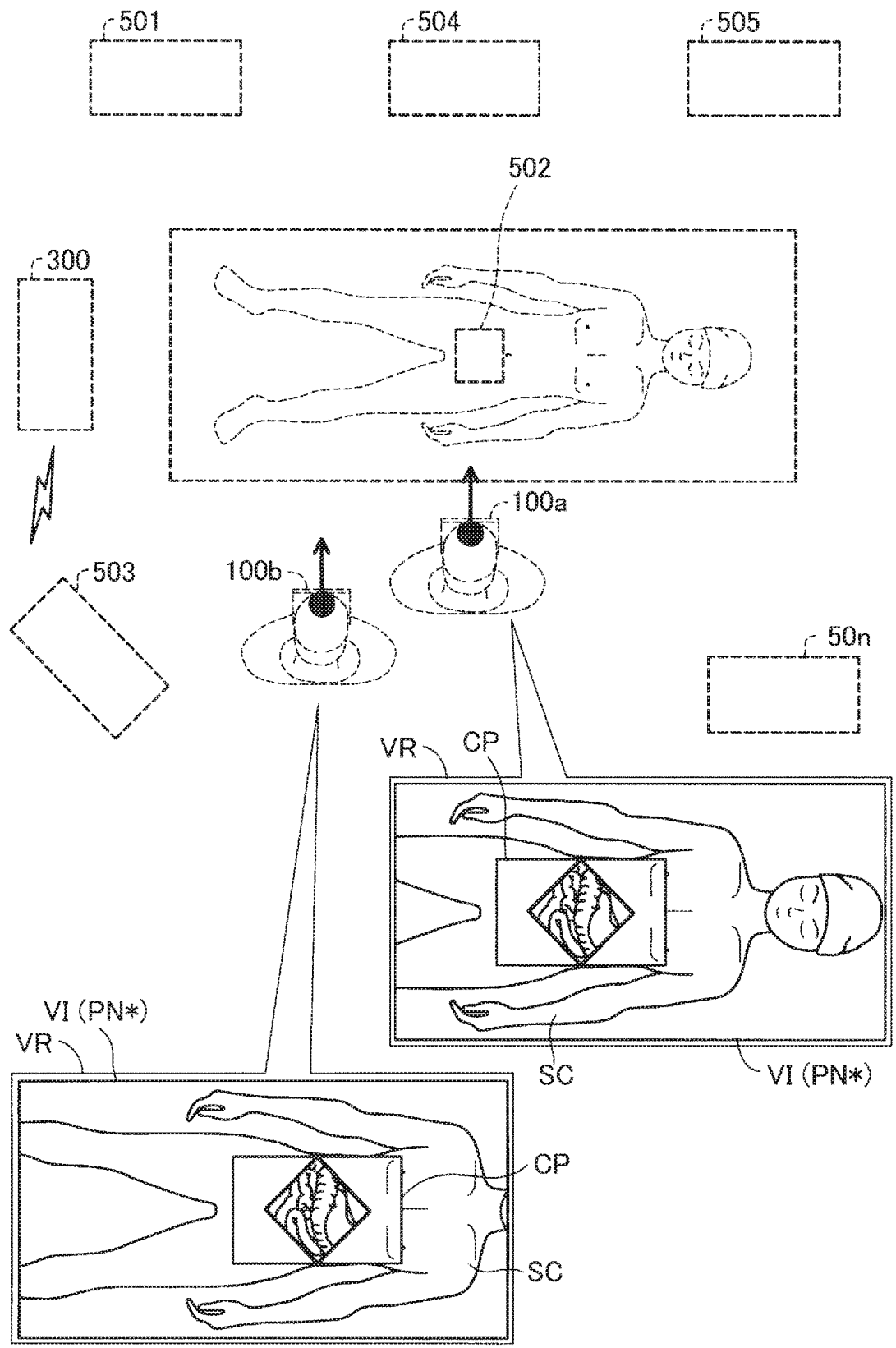
FIG. 12 is a view illustrating a state in which the presentation information is displayed as a virtual image on a plurality of head mounted displays.

FIG. 12 is a view illustrating a state in which the presentation information PN* is respectively displayed as a virtual image on the plurality of head mounted displays 100a and 100b. The aforementioned display processing is performed by the image processing unit 160 of the head mounted display 100a that receives the presentation information PN* transmitted from the second input/output unit 371 via the interface 180 or the wireless communication unit 132. As a result, image light guided to both eyes of the user of the head mounted display 100a is focused on the retinas of the user, and thus the user of the head mounted display 100a can see the presentation information PN* as a virtual image VI in a visual field VR. The user can directly see a patient lying on the operating table (an outside scene SC) through the right optical image display unit 26 and the left optical image display unit 28. Similarly, the aforementioned display processing is performed by the image processing unit 160 of the head mounted display 100b that receives the presentation information PN* transmitted from the second input/output unit 372, and the user of the head mounted display 100b can see the presentation information PN* as the virtual image VI in the visual field VR. In the example illustrated in FIG. 12, the medical apparatus information CP acquired from the medical apparatus 502 for photographing a still image and a moving image of an operated part is displayed in the virtual image VI (PN*) seen by the user of the head mounted display 100a and the user of the head mounted display 100b.

Figure 13:
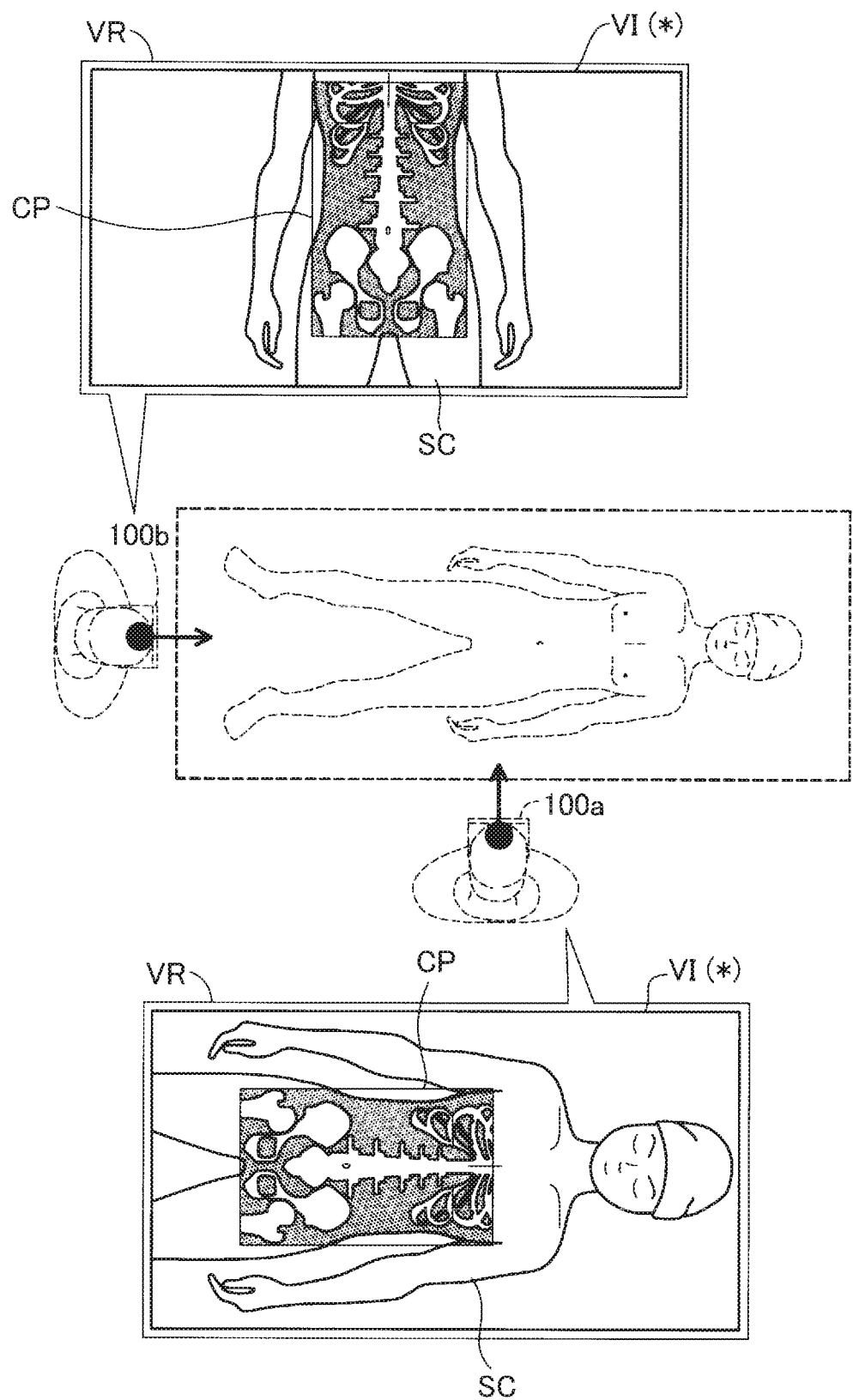
FIG. 13 is a view illustrating a state in which the presentation information is displayed as a virtual image on the plurality of head mounted displays that are positioned in different places.

FIG. 13 is a view illustrating a state in which the presentation information PN* is displayed as virtual images on the plurality of head mounted displays 100a and 100b that are positioned in different places. As illustrated in FIG. 13, the second input/output units 370 (the second input/output units 371 to 37n) of the information processing apparatus 300 may perform a fitting process in such a manner that an orientation and a size of the image contained in the presentation information coincide with an orientation and a size of a target object contained in the outside scene SC. For example, the target object is the body of a patient or a part of the body in a medical location. Hereinafter, the fitting process will be described with reference to the second input/output unit 371. In step S118 of the presentation information generating process (refer to FIG. 6), the second input/output unit 371 converts the image contained in the presentation information PN* as per the video signal specification of the head mounted display 100a, and then performs the following procedures d1 to d5.

(d1) The second input/output unit 371 instructs the head mounted display 100a to photograph an outside scene image using the camera 61, and acquires the photographed outside scene image.

(d2) The second input/output unit 371 extracts characteristics of the target object contained in the outside scene image using the following image recognition methods 1 and 2. The methods 1 and 2 may be combined.

1. An edge (characteristics) of the target object is detected
2. A marker (characteristics) which is attached to the target object in advance is detected. Various types of markers can be used as the marker attached to the object. For example, a tape, a seal, a magic marker, a laser marker, and a magic tape (registered trademark) can be used. The number of markers attached to the target object is arbitrarily adjusted.

(d3) The second input/output unit 371 extracts the characteristics of the target object by recognizing the image contained in the received presentation information. At this time, the second input/output unit 371 can use the same image recognition methods as the aforementioned methods 1 and 2.

(d4) The second input/output unit 371 compensates the image CP contained in the presentation information PN* in such a manner that the characteristics of the outside scene image extracted in the procedure d2 are positioned in the same place in which the characteristics of the presentation information extracted in the procedure d3 are positioned. Specifically, when the method 1 is used in the procedures d2 and d3, the second input/output unit 371 at least enlarges, reduces, rotates, reverses, trims, or distorts the image CP contained in the presentation information PN*, or removes noise from the image CP in such a manner that a contour and a characteristic portion of the edge of the outside scene image are positionally aligned with a contour and a characteristic portion of the edge of the presentation information. Here, when the target object is a living body, the characteristic portion is a contour of an incised skin, a contour of an internal organ, a joint, distal ends of limbs, a blood vessel, a bone, and the like. In contrast, when the method 2 is used in the procedures d2 and d3, the second input/output unit 371 at least enlarges, reduces, rotates, reverses, trims, or distorts the image CP contained in the presentation information PN*, or removes noise from the image CP in such a manner that the marker of the outside scene image is positionally aligned with the marker of the presentation information.

In this manner, the second input/output units 370 (the second input/output units 371 to 37n) recognize the image in the direction of the visual field of the user of the head mounted display 100 (the head mounted display apparatus), and thus the second input/output units 370 extract the characteristics of the object contained in the outside scene and compensates the presentation information generated by the generation unit 360 based on the extracted characteristics. For this reason, when the presentation information contains the invisible part information such as a CT image, an MRI image, or an X-ray image, it is possible to align the invisible part information with the object (for example, the body of a patient) contained in the outside scene. As a result, it is possible to improve convenience of the user of the head mounted display 100. Since the fitting processing is executed in the second input/output unit 370 connected to the specific head mounted display 100, a processing load is not applied to the second input/output units 370 connected to the other head mounted displays 100. Furthermore, since the head mounted display 100 can receive the presentation information that undergoes the fitting processing, the image processing unit 160 of the head mounted display 100 may display the received presentation information as it is. As a result, it is possible to simplify the configuration of the head mounted display 100.

As described above, when the operation mode of the generation unit 360 is the "first mode", the generation unit 360 generates the common presentation information PN* that contains at least the medical apparatus information selected by the user of the head mounted display 100 (that is, the specific image display apparatus) in which the inter-apparatus relationship of the management table 382 is a "master". The second input/output units 370 (presentation units) output the generated common presentation information PN* to the plurality of head mounted displays 100a to 100n (the image display apparatuses) which are respectively connected to the second input/output units 371 to 37n. As a result, the information processing apparatus 300 can control display on the plurality of head mounted displays 100a to 100n based on the selection of the user of the specific head mounted display 100.

A-4-2. Second Mode (Initial Process):

When the operation mode is the "second mode" in step S100 of the presentation information generating process (refer to FIG. 6) (step S100: the second mode), the generation unit 360 sets a variable i used in the presentation information generating process to "1" (step S120). Thereafter, the generation unit 360 refers to an i-th entry of the management table 382 (step S122). The generation unit 360 acquires an "identifier" and a "role" which are stored in the i-th entry of the management table 382 (step S124).

Hereinafter, the head mounted display 100 having the identifier acquired in step S124 is also referred to as a "head mounted display 100i". The head mounted display 100i indicates the head mounted display 100 that is currently under the processing in the initial process. For example, when the variable i is 1, the head mounted display 100i indicates the head mounted display 100a of the operating surgeon, which has the identifier of 1 and is stored in the first entry E01 of the management table 382.

In step S126 of the presentation information generating process (refer to FIG. 6), the generation unit 360 specifies the medical apparatus 500 based on the role of the user of the head mounted display 100i. Specifically, when the generation unit 360 carries out the "role" acquired in step S124, the generation unit 360 specifies the medical apparatus 500 that the user of the head mounted display 100i has to check. The medical apparatus 500 is specified based on a practice in a medical location. For example, when the role is an operating surgeon, an apparatus which acquires the invisible part information such as a CT image or an X-ray image is specified as the medical apparatus 500. When the role is an anesthesiologist, each of a blood pressure meter, an electrocardiogram, an airway pressure meter, a ventilation meter, a capnogram and a pulse oximeter is specified as the medical apparatus 500. The information processing apparatus 300 may store a table in the external storage apparatus 380 in advance, in which the role and the medical apparatus 500 necessary for the role are stored in association with each other.

After the medical apparatus 500 is specified, the generation unit 360 generates the presentation information PNi to be transmitted to the head mounted display 100i using the medical apparatus information that is acquired from the medical apparatus 500 specified in step S126 among the medical apparatus information of the medical apparatuses 501 to 50n, which the first input/output units 311 to 31n acquire in step S128. The generation unit 360 generates the presentation information in the same method as described with reference to FIGS. 7A, 7B, and 8. Thereafter, the generation unit 360 stores the generated presentation information PNi in the operation record 384.

In step S130, the generation unit 360 transmits the presentation information PNi generated in step S124 to a second input/output unit 370i to which the head mounted display 100i is connected. The second input/output unit 370i converts an image contained in the received presentation information PNi as per a video signal specification of the head mounted display 100i. At this time, the second input/output unit 370i may execute the fitting process. The detail is the same as described in step S118.

Figure 14:
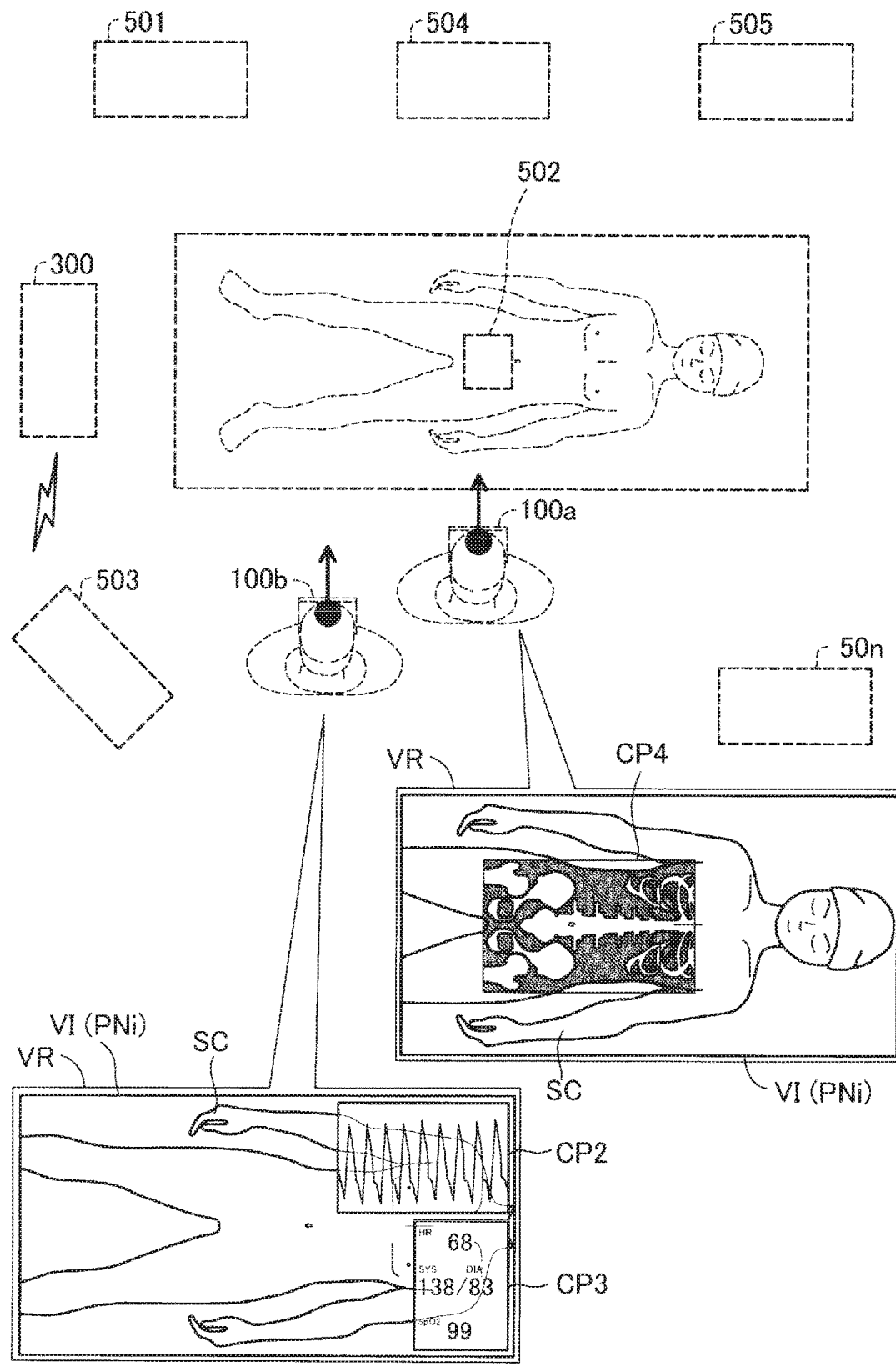
FIG. 14 is a view illustrating a state in which the presentation information is displayed as a virtual image on the plurality of head mounted displays after steps S122 to S134 are executed two times.

FIG. 14 is a view illustrating a state in which the presentation information PNi is displayed as virtual images on the plurality of head mounted displays 100a and 100b after steps S122 to S134 are executed two times. The aforementioned display processing is performed by the image processing unit 160 of the head mounted display 100i that receives the presentation information PNi via the interface 180 or the wireless communication unit 132. As a result, the user of the head mounted display 100i can see the presentation information PNi as a visual image, which contains the medical apparatus information acquired from the medical apparatus 500 based on the role of the user. In an example illustrated in FIG. 14, the medical apparatus information CP4 acquired from the medical apparatus 500, which an operating surgeon has to check, is displayed as a virtual image VI (i) that the user of the head mounted display 100a sees. The medical apparatus information CP2 and CP3 acquired from the medical apparatus 500, which a first assistant has to check, is displayed as the virtual image VI (i) that the user of the head mounted display 100b sees.

The generation unit 360 increments the variable i in step S132 of the presentation information generating process (refer to FIG. 6). Thereafter, the generation unit 360 determines whether the variable i is equal to or greater than n (step S134). The fact that the variable i is smaller than n (step S134: NO) means that a part of the head mounted displays 100 do not end the initial process among the head mounted displays 100 which are respectively connected to the second input/output units 370. For this reason, the generation unit 360 transfers the process to step S122 to continuously execute the initial process. In contrast, the fact that the variable i is equal to or greater than n (step S134: YES) means that the initial processes for the entirety of the head mounted displays 100 are ended. For this reason, the generation unit 360 transfers the process to an individual process in step S136.

As described above, when the operation mode of the generation unit 360 is the "second mode", the generation unit 360 repeatedly executes the steps S122 to S134 in the initial process. Accordingly, the generation unit 360 generates plural pieces of the presentation information PNi that contain at least the medical apparatus information which is acquired from the medical apparatuses 500 based on the respective roles of the users of the plurality of head mounted displays 100i (100a to 100n). In addition, the second input/output units 370 (the presentation units) sequentially output the plural pieces of generated presentation information PNi to the plurality of head mounted displays 100a to 100n (the image display apparatuses) which are respectively connected to the second input/output units 371 to 37n. As a result, the information processing apparatus 300 can individually control display on the plurality of head mounted displays 100a to 100n based on the role of each user of the head mounted display 100, and it is possible to improve convenience of each user of the head mounted display 100.

A-4-3. Second Mode (Individual Process):

In the individual process, based on a request from the head mounted display 100, the generation unit 360 generates the presentation information that contains the medical apparatus information acquired from the requested medical apparatus 500 and the information acquired from information sources other than the requested medical apparatus 500.

The generation unit 360 determines whether a request for an information source selection is received from the head mounted display 100 in step S136 of the presentation information generating process (refer to FIG. 6). The request for an information source selection is the same as the requests a1 to a6 which are described in step S112. When the request for an information source selection is not received (step S136: not received), the generation unit 360 transfers the process to the step S136, and waits for the request for an information source selection.

In contrast, when the request for an information source selection is received (step S136: received), The generation unit 360 acquires an identifier of the head mounted display 100i contained in the request for an information source selection, information for specifying the information source, and information for specifying the information in the information source (step S128). Furthermore, when the current position information and the orientation information are inserted as the information for specifying the information source, the generation unit 360 compares the current position information and the orientation information with position information acquired from the entirety of other medical apparatuses 500, and the generation unit 360 specifies "the medical apparatus 500, the display unit of which the user can hardly see". Here, similarly to in step S114, the generation unit 360 may combine the current position information and the orientation information with a movement of the head of the user of the head mounted display 100. The head mounted display 100i indicates the head mounted display 100 (that is, the head mounted display 100 that is currently under the processing) which is a source of issuing the request for an information source selection.

The generation unit 360 accesses the designated information source, and acquires the designated information in step S140. The generation unit 360 generates the presentation information PNi for the head mounted display 100i using the acquired information, and stores the generated presentation information PNi in the operation record 384. The generation unit 360 generates the presentation information in the same method as described with reference to FIGS. 7A, 7B, and 8. Thereafter, the generation unit 360 stores the generated presentation information PNi in the operation record 384.

In step S142, the generation unit 360 transmits the presentation information PNi generated in step S140 to the second input/output unit 370i to which the head mounted display 100i is connected. The second input/output unit 370i converts an image contained in the received presentation information PNi as per the video signal specification of the head mounted display 100i. At this time, the second input/output unit 370i may execute the fitting process. The detail is the same as described in step S118.

The aforementioned display processing is performed by the image processing unit 160 of the head mounted display 100i that receives the presentation information PNi via the interface 180 or the wireless communication unit 132. As a result, the user of the head mounted display 100i, which transmits the request for an information source selection, can see a virtual image of the presentation information PNi that includes the information acquired from the information source designated in the request for an information source selection.

As described above, when the operation mode of the generation unit 360 is the "second mode", the generation unit 360 executes the individual process. Accordingly, the generation unit 360 generates the plural pieces of presentation information PNi that contain at least the medical apparatus information which is selected by each user of the plurality of head mounted displays 100i (100a to 100n). The second input/output units 370 (the presentation units) sequentially output the plural pieces of generated presentation information PNi to the plurality of head mounted displays 100a to 100n (the image display apparatuses) which are respectively connected to the second input/output units 371 to 37n. As a result, the information processing apparatus 300 can individually control display on the plurality of head mounted displays 100a to 100n based on the role of each user of the head mounted display 100.

As described above, in the information processing apparatus 300 of First Embodiment, the generation unit 360 generates the presentation information PN using the plural pieces of medical apparatus information acquired by the first input/output units 310 (acquisition units and the first input/output units 311 to 31n), and thus the information processing apparatus 300 can unify the information (the medical apparatus information) of various medical apparatuses 500 (the medical apparatuses 501 to 50n) which are connected to the first input/output units 310 of the information processing apparatus 300. The second input/output units 370 (the presentation units) output the generated presentation information PN to the plurality of head mounted displays 100a to 100n (the image display apparatuses), respectively, and thus the second input/output units 370 can control display on the plurality of head mounted displays 100a to 100n, respectively. As a result, it is possible to unify the information of various medical apparatuses 500, and it is possible to realize the information processing apparatus 300 that can control the display on the plurality of head mounted displays 100a to 100n.

Furthermore, the generation unit 360 has the first mode in which the common presentation information PN* is generated from the unified medical apparatus information, which is common to the plurality of head mounted displays 100a to 100n (the image display apparatuses), and the second mode in which the plural pieces of presentation information PNi are generated to respectively correspond to the plurality of head mounted displays 100a to 100n. For this reason, the generation unit 360 uses the modes separately, and thus the information processing apparatus 300 can control the display on the plurality of head mounted displays 100a to 100n.

As described above, the information processing system 1000 of First Embodiment can unify the information (the medical apparatus information) of various medical apparatuses 500 (the medical apparatuses 501 to 50n) in the information processing apparatus 300, and it is possible to realize the information processing system 1000 that can control the display on the plurality of head mounted displays 100a to 100n (the head mounted display apparatuses).

A-5. Additional Process:

In the presentation information generating process (refer to FIG. 6), the following additional processes may be further executed. The additional processes may be added independently or may be combined together.

A-5-1. Additional Process 1:

In an additional process 1, the information processing apparatus 300 performs a color conversion process for the presentation information. Specifically, the second input/output unit 370, which receives the presentation information from the generation unit 360, causes the camera 61 of the head mounted display 100 to acquire an outside scene image. The second input/output unit 370 carries out the color conversion process so as to improve visibility of the image contained in the presentation information based on brightness, contrast, chroma, and color of the acquired outside scene image. For example, the second input/output unit 370 can perform the color conversion process in which the color of the image contained in the presentation information is converted into a complementary color of the color of the outside scene image.

In this manner, the additional process 1 can further improve visibility of the virtual image VI for the user of the head mounted display 100.

A-5-2. Additional Process 2:

An additional process 2 enables the information processing apparatus 300 to realize a so-called stabilizer function that suppresses the flickering of the virtual image VI incident to a small shake of the head of the user of the head mounted display 100. Specifically, the second input/output unit 370, which receives the presentation information from the generation unit 360, repeatedly performs the fitting process described in the procedures d1 to d4, and the transmission of the presentation information described in steps S118, S130, and S142 of the presentation information generating process at every predetermined time. Accordingly, the following is repeatedly performed at every predetermined time: the photographing of the outside scene image, and the compensation and the display of the image contained in the presentation information. As a result, the presentation information can be displayed as the virtual image VI so as to trace the movement over time of the head of the user.

However, when the presentation information traces a slight movement or a fluctuation of the head of the user of the head mounted display 100, and thus the presentation information is frequently changed, there is a problem in that eyestrain of the user is induced and concentration of the user is disturbed. Therefore, the second input/output unit 370 may perform processes described in the following procedures e1 and e2 between the procedure d1 and the procedure d2.

(e1) The second input/output unit 370 calculates the amount of change in RGB histogram between the outside scene image photographed in the procedure c1 and the outside scene image photographed in the procedure d1 in the fitting process that is executed at the previous cycle.

(e2) When the amount of change calculated in the procedure f1 exceeds a predetermined threshold value, the second input/output unit 370 continuously performs the processes subsequent to the procedure d2.

In this manner, in the additional process 2, when there is a small amount of change between the outside scene image in the fitting process executed at the previous cycle and the outside scene image in the fitting process currently being executed, that is, when the movement of the head of the user of the head mounted display 100 is very small, the second input/output unit 370 does not compensate the image contained in the presentation information. As a result, since the presentation information can be prevented from tracing a very small movement or a fluctuation of the head of the user of the head mounted display 100, and can be prevented from frequently being changed, it is possible to suppress eyestrain or deterioration of concentration of the user. A configuration may be adopted in which the user can turn on and off the stabilizer function.

A-5-3. Additional Process 3:

In an additional process 3, the information processing apparatus 300 changes a size of the image, which is contained in the presentation information and is displayed as the virtual image VI, based on a distance between the image display unit 20 of the head mounted display 100 and an object that is present in the direction of the visual field of the user. Specifically, the second input/output unit 370, which receives the presentation information from the generation unit 360, can perform processes described in the following procedures f1 to f3 instead of the fitting process described in the procedures d1 to d4. When this process is carried out, the head mounted display 100 is configured to further include a distance measurement sensor. The distance measurement sensor is a sensor that uses reflected light to acquire the distance between the object present in the direction of the visual field of the user and the image display unit 20. For example, the distance measurement sensor can be arranged in the vicinity of the camera 61.

(f1) The second input/output unit 370 periodically acquires a measurement value of the distance measurement sensor of the head mounted display 100.

(f2) The second input/output unit 370 determines an enlargement ratio (or a reduction ratio) based on the acquired measurement value of the distance measurement sensor.

(f3) The second input/output unit 370 at least enlarges, reduces, rotates, reverses, trims, or distorts the image contained in the presentation information, or removes noise from the image using the determined enlargement or reduction ratio.

In this manner, according to the additional process 3, the second input/output unit 370 can change the size of the presentation information to be displayed as the virtual image VI based on the distance between the object present in the direction of the visual field of the user of the head mounted display 100 and the image display unit 20. For this reason, it is possible to improve convenience of each user of the head mounted display 100.

B. Second Embodiment

In a second embodiment of the invention, a configuration will be described in which the generation unit 360 can generate combined information. Hereinafter, only portions having configurations and operations different from those of First Embodiment will be described. In the drawings, the same reference signs as those of First Embodiment will be assigned to portions with the same configurations as those of First Embodiment. The detailed description will be omitted.

B-1. Configuration of Information Processing System:

A schematic configuration of an information processing system 1000a according to Second Embodiment is the substantially same as that of First Embodiment illustrated in FIG. 1. However, the information processing system 1000a of Second Embodiment includes an information processing apparatus 300a instead of the information processing apparatus 300.

Figure 15:
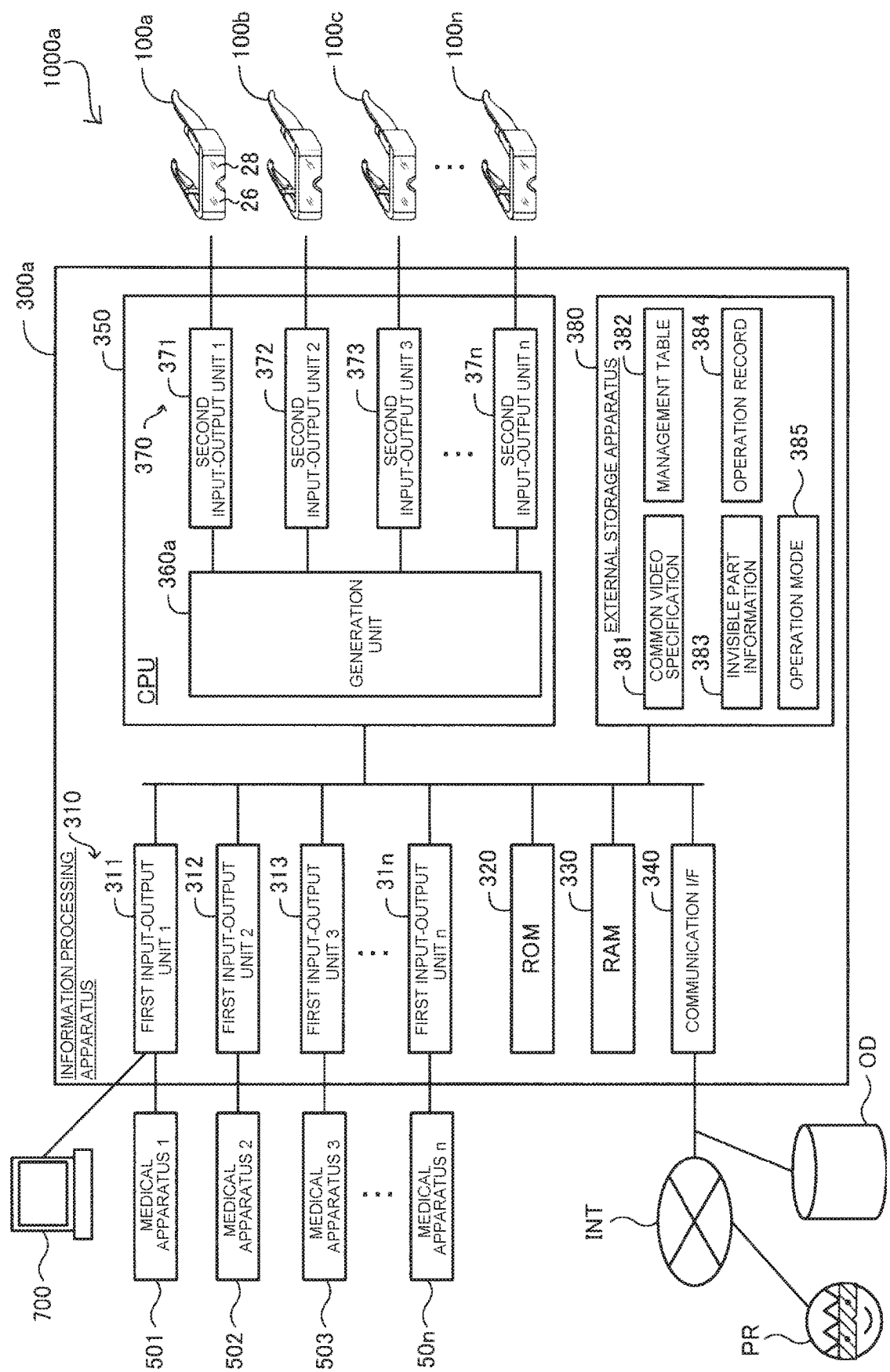
FIG. 15 is a block diagram illustrating a functional configuration of an information processing apparatus according to Second Embodiment.

B-2. Configuration of Information Processing Apparatus:

FIG. 15 is a block diagram illustrating a functional configuration of the information processing apparatus 300a according to Second Embodiment. Second Embodiment is different from First Embodiment illustrated in FIG. 2 in that the information processing apparatus 300a includes a generation unit 360a instead of the generation unit 360. When the operation mode is the "second mode", the generation unit 360a executes a combined information generating process to be described later in parallel with the presentation information generating process. The combined information generating process is a process in which the generation unit 360a generates the combined information obtained by combining together the presentation information of the entirety of the head mounted displays 100 (the head mounted displays 100a to 100n) that are respectively connected to the second input/output units 370.

B-3. Configuration of Head Mounted Display Apparatus:

The schematic configuration of the head mounted display 100 according to Second Embodiment is the same as that of First Embodiment illustrated in FIG. 5.

B-4. Presentation Information Generating Process:

Procedures of the presentation information generating process according to Second Embodiment is the same as that of First Embodiment illustrated in FIG. 6.

B-5. Additional Process:

Even in the presentation information generating process of Second Embodiment, the same additional processes as those of First Embodiment may be executed as described in the "A-5-1 Addition Process 1" to the "A-5-3 Additional Process 3".

Figure 16:
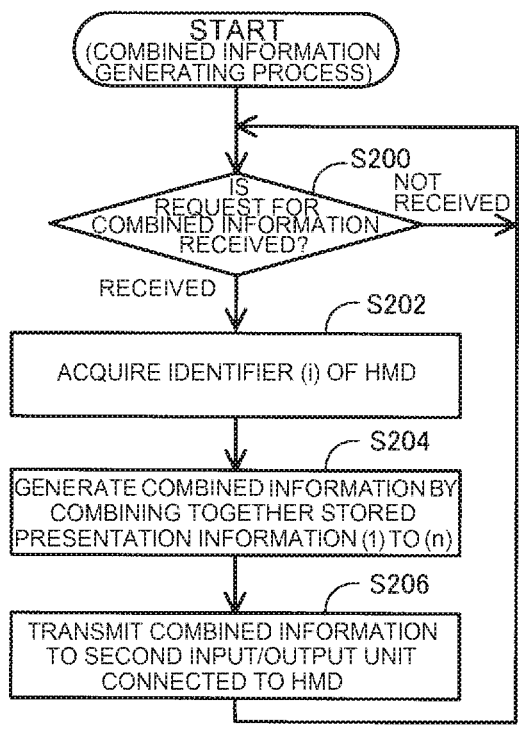
FIG. 16 is a flow chart illustrating procedures of combined information generating process.

B-6. Combine Information Generating Process:

FIG. 16 is a flow chart illustrating procedures of the combined information generating process. The combined information generating process is a process in which the combined information is generated to be displayed on the head mounted display 100. The generation unit 360a of the information processing apparatus 300a (refer to FIG. 15) executes the combined information generating process. In step S100 of the presentation information generating process (refer to FIG. 6), when the operation mode is the "second mode" (step S100: the second mode), the combined information generating process is executed in parallel with the initial process and the individual process described in FIG. 6.

The generation unit 360a determines whether a request for combined information is received from the head mounted display 100 (step S200). Here, the request for combined information is a request for transmission of the combined information, and is transmitted along with an identifier of the requesting head mounted display 100. When the request for combined information is not received (step S200: not received), the generation unit 360a transfers the process to step S200, and waits to receive the request for combined information.

In contrast, when the request for combined information is received (step S200: received), the generation unit 360a acquires an identifier of the requesting head mounted display 100i, which is contained in the request for combined information (step S202). Here, the head mounted display 100i indicates the head mounted display 100 (that is, the head mounted display 100 that is currently under the processing) which is a source of issuing the request for combined information.

The generation unit 360a accesses the operation record 384 in step S204. The generation unit 360a acquires the latest presentation information which the generation unit 360a generates for the entirety of the head mounted displays 100 (the head mounted displays 100a to 100n) that are respectively connected to the second input/output units 370. The latest presentation information can be determined based on "a date and time of the information generation" that are stored in the operation record 384 in association with the presentation information. Here, the presentation information of the requesting head mounted display 100i may not be acquired. The generation unit 360a generates the combined information by combining together plural pieces of the acquired presentation information.

Figure 17:
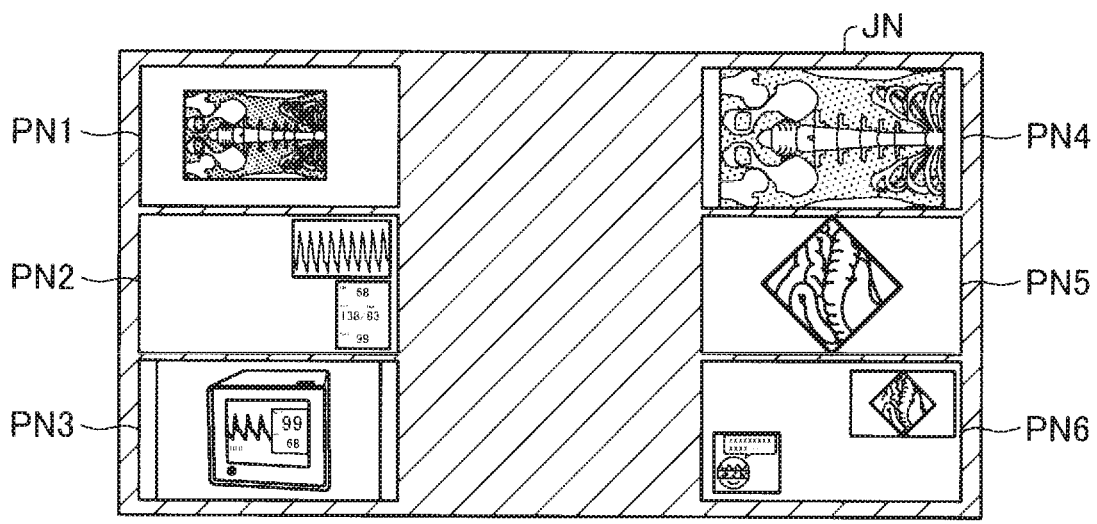
FIG. 17 is a view describing a method of generating the combined information.

FIG. 17 is a view describing a method of generating the combined information. The generation unit 360a performs processes illustrated in the following procedures g1 to g4 on the plural pieces of acquired presentation information.

(g1) The generation unit 360a determines a reduction ratio of the presentation information based on a total number of the acquired presentation information and resolution that is stored in the common video specification 381.

(g2) The generation unit 360a reduces the image contained in the i-th presentation information (the presentation information PNi) at the reduction ratio determined in the procedure g1.

(g3) The generation unit 360a arranges the image reduced in the procedure g2 at a position at which the reduced image does not overlap with other images, and the reduced image is overwritten and saved as combined information JN.

(g4) The generation unit 360a increments the variable i, and repeatedly performs the procedures g2 and g3 until "i is equal to or larger than a total number of the acquired presentation information" is met.

(g5) The generation unit 360a executes the same procedures as described in c1 and c2 with respect to a margin (indicated by a hatched line in FIG. 17) in which the image for the presentation information among the combined information JN is not arranged. Dummy dot data is inserted in the margin, or an enable signal is adjusted.

(g6) The generation unit 360a converts the image contained in the generated combined information JN as per the video signal specification defined in the common video specification 381.

FIG. 17 illustrates an example of the combined information JN in which six presentation information PN1 to PN6 generated in this manner are respectively arranged at positions at which six presentation information does not overlap with each other.

In step S206 of the combined information generating process (refer to FIG. 16), the generation unit 360a transmits the combined information JN generated in step S204 to the second input/output unit 370i to which the head mounted display 100i is connected, and then transfers the process to step S200. The second input/output unit 370i converts the image contained in the received presentation information PNi as per the video signal specification of the head mounted display 100i.

Figure 18:
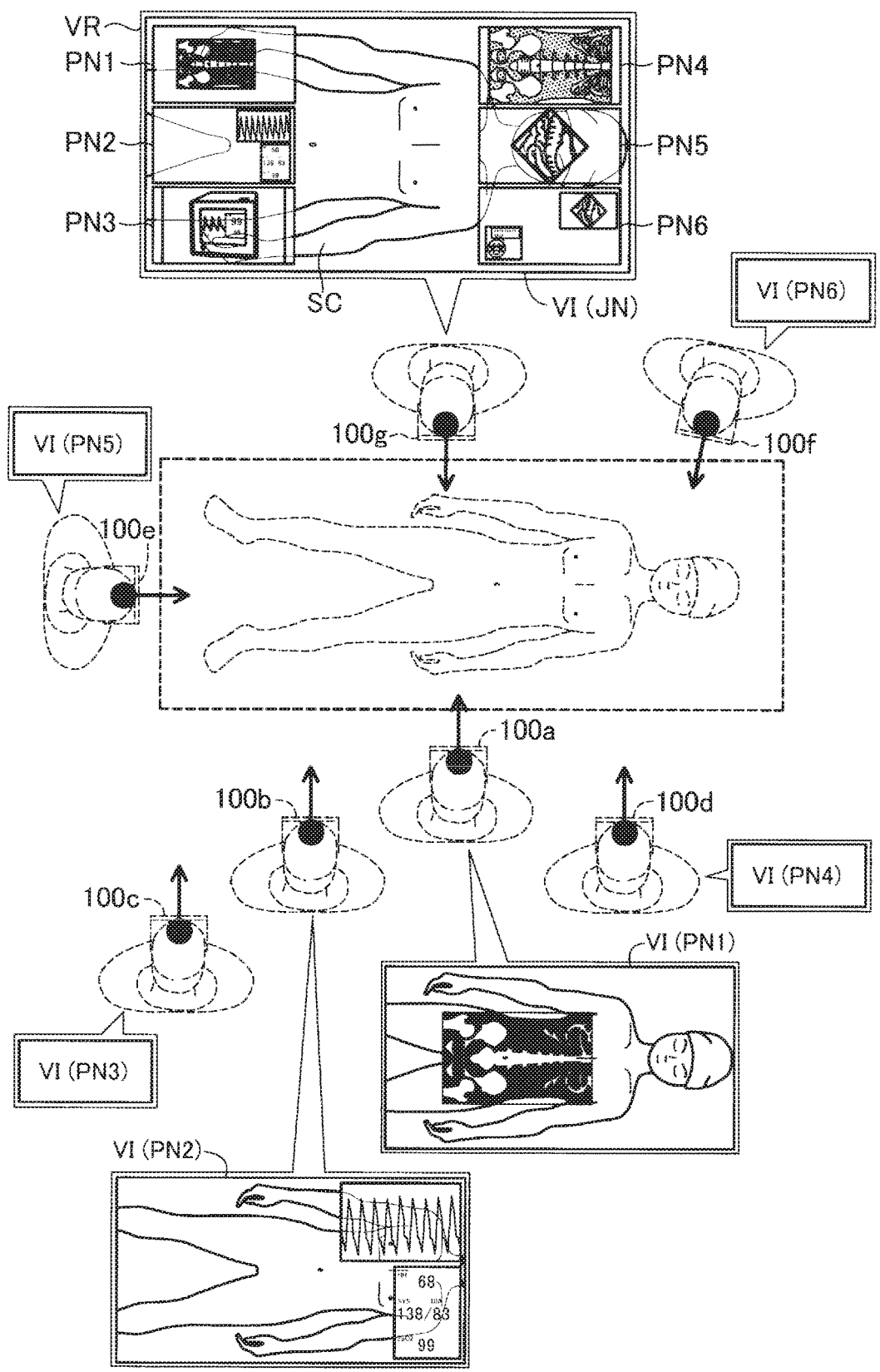
FIG. 18 is a view illustrating a state in which the combined information is displayed as a virtual image on the head mounted display.

FIG. 18 is a view illustrating a state in which the combined information JN is displayed as a virtual image on the head mounted display 100i. The aforementioned display process is performed by the image processing unit 160 of the head mounted display 100i that receives the combined information JN transmitted from the second input/output unit 370i via the interface 180 or the wireless communication unit 132. As a result, image light guided to both eyes of the user of the head mounted display 100i is focused on the retinas of the user, and thus the user of the head mounted display 100i can see the combined information JN as the virtual image VI in the visual field VR. In the example illustrated in FIG. 18, the combined information JN of the presentation information PN1 to PN6 for the respective head mounted displays 100a to 100f is displayed as the virtual image VI in the visual field VR of the user of the head mounted display 100g. Due to limitation of space, the presentation information PN3 to PN6 is not illustrated in FIG. 18.

As described above, the generation unit 360a of Second Embodiment combines the plural pieces of presentation information PNi generated in the presentation information generating process to generate the combined information JN. The second input/output unit 370 (the presentation unit) outputs the generated combined information JN to the specific head mounted display 100i (the image display apparatus) that issues the request for combined information. As a result, the user of the specific head mounted display 100i can understand what presentation information PN is displayed on the plurality of head mounted displays 100a to 100n (the image display apparatuses) which are connected to the information processing apparatus 300. In addition, it is possible to improve convenience of the user of the specific head mounted display 100i.

C. Third Embodiment

A third embodiment of the invention describes a configuration in which the user of the head mounted display is guided through a series of predetermined steps, and in which the guiding steps can be changed in real time based on the medical apparatus information. Hereinafter, only portions having configurations and operations different from those of First Embodiment will be described. In the drawings, the same reference signs as those of First Embodiment will be assigned to portions with the same configurations as those of First Embodiment described above. The detailed description will be omitted.

C-1. Configuration of Information Processing System:

A schematic configuration of an information processing system 1000b according to Third Embodiment is the substantially same as that of Second Embodiment illustrated in FIG. 1. However, the information processing system 1000b of Second Embodiment includes an information processing apparatus 300b instead of the information processing apparatus 300.

Figure 19:
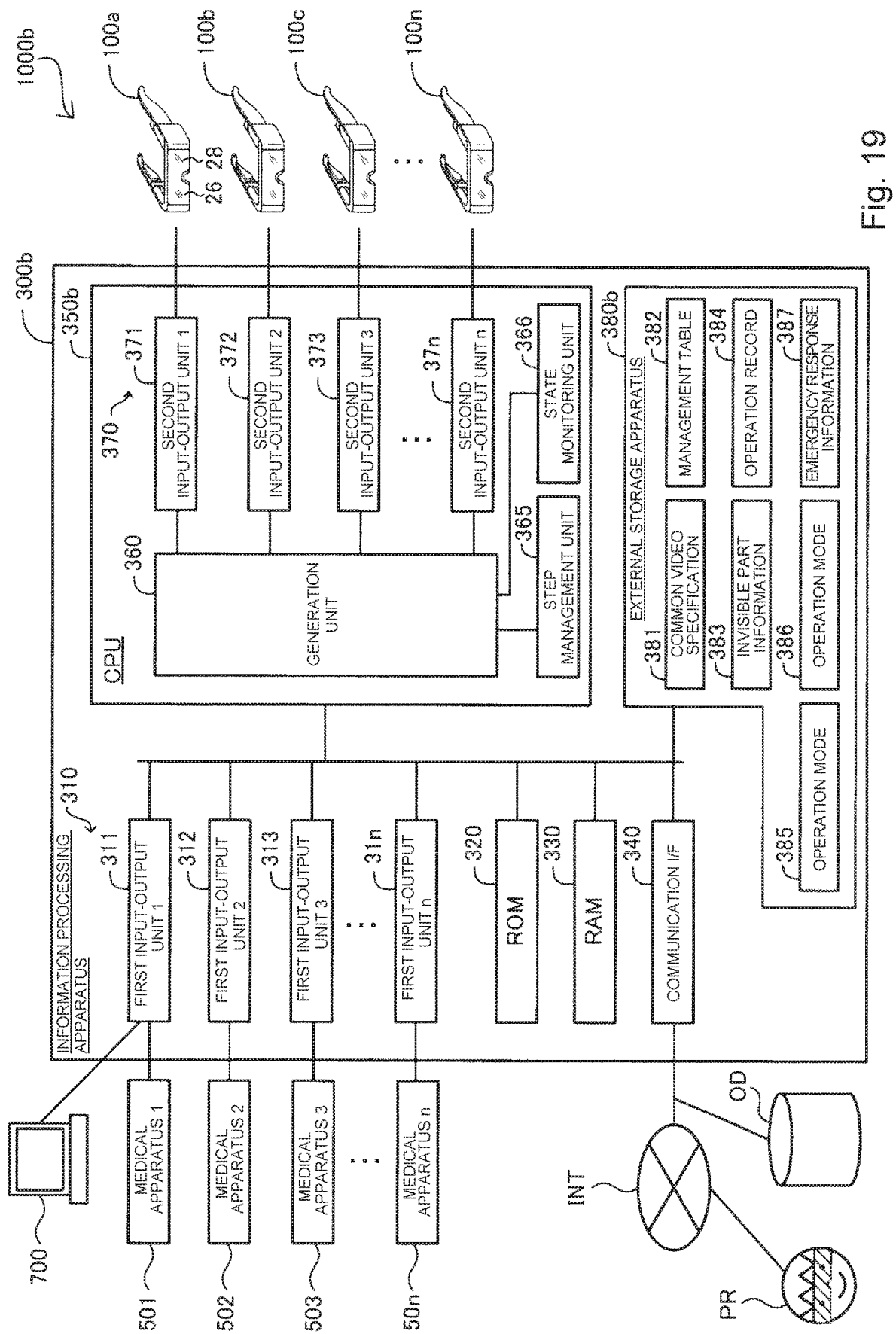
FIG. 19 is a block diagram illustrating a functional configuration of an information processing apparatus according to Third Embodiment.

C-2. Configuration of Information Processing Apparatus:

FIG. 19 is a block diagram illustrating a functional configuration of the information processing apparatus 300b according to Third Embodiment. Third Embodiment is different from First Embodiment illustrated in FIG. 2 in that the information processing apparatus 300b includes a CPU 350b instead of the CPU 350, and includes an external storage apparatus 380b instead of the external storage apparatus 380. The CPU 350b includes a generation unit 360b instead of the generation unit 360, and further includes a step management unit 365.

Processes in the presentation information generating process executed by the generation unit 360b are partially different from those of First Embodiment illustrated in FIG. 6. The step management unit 365 executes a step management process to be described later in parallel with the presentation information generating process executed by the generation unit 360. The step management process is a process in which the step management unit 365 transmits to the generation unit 360b a series of steps through which the user of the head mounted display 100 is guided, and in which the steps are changed based on a state of a patient estimated from the medical apparatus information.

An external storage apparatus 380b further includes step information 386 and emergency response information 387 in addition to all the information described in First Embodiment.

Figures 20, 21:
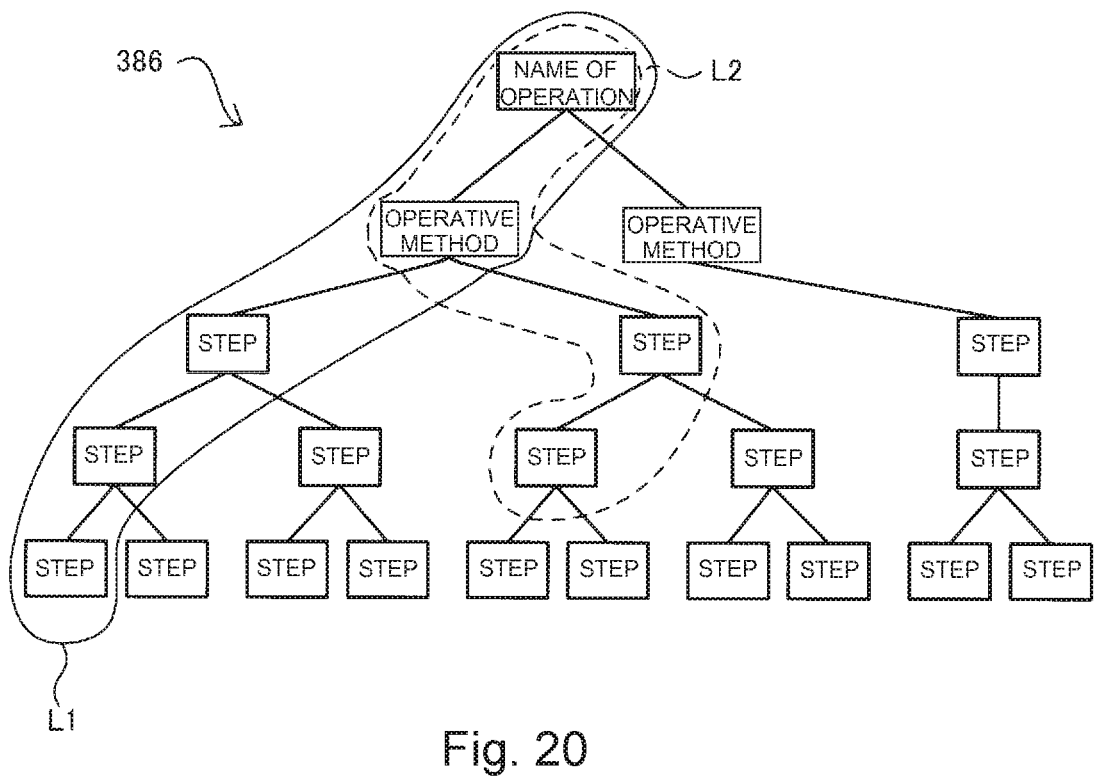
FIG. 20 is a schematic diagram illustrating an example of step information.
FIG. 21 is a table illustrating an example of emergency response information.

FIG. 20 a schematic diagram illustrating an example of the step information 386. The step information 386 in the embodiment is a table (or a database configured to have a plurality of tables) in which a series of steps for each of various operations are stored in advance. In the step management process, the step information 386 is referenced so as to guide the user of the head mounted display 100 through the steps. For illustrative purposes, FIG. 20 illustrates only a single operation, and a specific name of operation, a name of operative method, and content of steps will not be illustrated. A name for specifying an operation is stored in the "name of operation". A name for specifying an operative method is stored in the "name of operative method". Since an operation may be performed in a plurality of different operative methods, steps for the operation are specified based on the combination of the name of operation and the operative method. Content of series of steps specified by the name of operation and the operative method are sequentially stored in the "step". Since a part of steps for an operation are differently executed based on symptoms and a state of a patient, the branched steps are present in the example illustrated in FIG. 20. In the presentation information generating process (refer to FIG. 6), when the second mode is realized to generate the plural pieces of presentation information, the step information 386 is configured to include a table and the like, in which a series of steps are stored for each role in various operations.

FIG. 21 is a table illustrating an example of the emergency response information 387. The emergency response information 387 of the embodiment stores operative method, conditions, symptoms, and emergency responses in association with each other in advance. In the step management process, the emergency response information 387 is referenced so as to change steps through which the user of the head mounted display 100 is guided. A name for specifying an operative method is stored in an "operative method". The operative method is used so as to be associated with the "operative method" in the step information 386. Conditions for judging the medical apparatus information is stored in the "condition". A name is stored in the "symptom", and the name indicates symptoms that are estimated to occur in a patient when the medical apparatus information satisfies the conditions stored in the "condition". Treatments for resolving or mitigating the symptoms of the patient are stored in the "emergency response".

C-3. Configuration of Head Mounted Display Apparatus:

The schematic configuration of the head mounted display 100 according to Third Embodiment is the same as that of First Embodiment illustrated in FIG. 5.

C-4. Presentation Information Generating Process:

Procedures of the presentation information generating process according to Third Embodiment are the same as those of First Embodiment illustrated in FIG. 6 except for the following points to be described below. A case where the presentation information generating process is executed in the first mode in which the common presentation information is generated will be described. In step S114 illustrated in FIG. 6, the generation unit 360b receives a "request (a7) for an operation procedure guide" as a request for an information source selection from the head mounted display 100. Thereafter, the generation unit 360b requests the step management unit 365 to execute the step management process. The request a7 may be issued independently or may be combined with the requests a1 to a6 of First Embodiment. In step S116, the generation unit 360b receives steps from the step management unit 365, and generates the presentation information PN* using the received information.

A case where the presentation information generating process is executed in the second mode in which the plural pieces of presentation information are generated will be described. In step S126 illustrated in FIG. 6, the generation unit 360b transmits a role of the user of the head mounted display 100i to the step management unit 365. Thereafter, the generation unit 360b transmits the role of the user to the step management unit 365, and requests the step management unit 365 to execute the step management process. In step S128, the generation unit 360b receives steps from the step management unit 365 based on the role of the user of the head mounted display 100i, and generates the presentation information PNi using the received information.

C-5. Additional Process:

Even in the presentation information generating process of Third Embodiment, the same additional processes as those of First Embodiment may be executed as described in the "A-5-1 Addition Process 1" to the "A-5-3 Additional Process 3".

Figure 22:
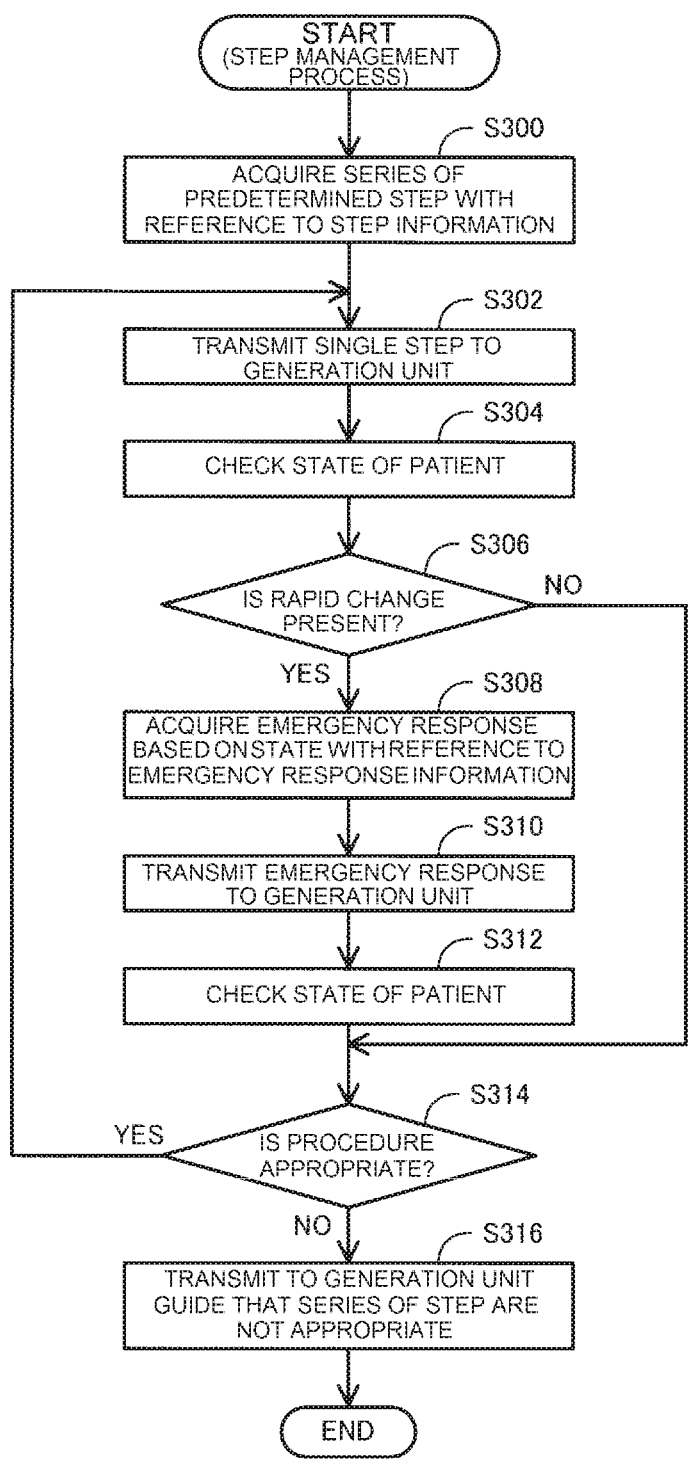
FIG. 22 is a flow chart illustrating procedures of a step management process.

C-6. Step Management Process:

FIG. 22 is a flow chart illustrating procedures of the step management process. The step management process is a process in which the step management unit transmits to the generation unit 360b steps through which the user of the head mounted display 100 is guided, and in which the steps are changed based on a state of a patient estimated from the medical apparatus information.

In step S300, the step management unit 365 acquires a series of predetermined steps with reference to the step information 386. Here, "the series of predetermined steps" mean a set of series of steps (indicated by solid line frame L1 in FIG. 20) which an operating surgeon, other doctors, or the like determines among the combinations of operations, the operative methods, and the steps stored in the step information 386 in advance. The series of predetermined steps may end in the middle of series of steps stored in the step information 386 (indicated by broken line frame L2 in FIG. 20). For example, when a doctor preferably selects the best steps while performing an operation in practicality and monitoring a state of the patient, the steps indicated by broken line frame L2 are scheduled.

When the presentation information generating process is executed in the first mode (in other words, when the generation unit 360b instructs that only the step management process be executed), and the steps based on the role of the user is stored in the step information 386, in step S300, the step management unit 365 acquires "a series of predetermined steps" for the role of the user of the head mounted display 100, the inter-apparatus relationship of which is a "master" in the management table 382 (refer to FIG. 4). In contrast, when the presentation information generating process is executed in the second mode (in other words, the role of the user and the execution of the step management process are instructed by the generation unit 360), in step S300, the step management unit 365 acquires "the series of predetermined steps" for the role of the user, which are received from the step information 386.

In step S302, the step management unit 365 acquires a single step from the series of steps acquired in step S300, and transmits the single step to the generation unit 360b. The generation unit 360b which receives the single step generates the presentation information PN* or the presentation information PNi for a guide to the single step in the presentation information generating process, and the generation unit 360b transmits the presentation information PN* or the presentation information PNi to the head mounted display 100.

The step management unit 365 checks a state of the patient in step S304. Specifically, the step management unit 365 acquires the entire medical apparatus information measured by the medical apparatus, which measures a state of the patient, via the first input/output units 310 (the acquisition units, and the first input/output units 311 to 31n).

In step S306, the step management unit 365 determines whether a rapid change occurs in the patient. Specifically, the step management unit 365 determines whether the entire medical apparatus information received in step S304 satisfies the "condition" stored in the emergency response information 387 in step S304. When the entire medical apparatus information does not satisfy the condition (step S306: NO), the step management unit 365 transfers the process to step S314. In contrast, when at least a single piece of medical apparatus information satisfies the condition (step S306: YES), the step management unit 365 transfers the process to step S308.

In step S308, the step management unit 365 acquires an emergency response based on a state of the patient with reference to the emergency response information 387. Specifically, the step management unit 365 refers to an entry, the medical apparatus information of which satisfies the "condition" among the emergency response information 387, and the step management unit 365 refers to the "emergency response" for the entry.

The step management unit 365 transmits content of the emergency response to the generation unit 360b in step S310. The aforementioned processes are executed in the same manner when the presentation information generating process is executed not only in the first mode but also in the second mode. The generation unit 360b which receives the emergency response generates the presentation information PN* or the presentation information PNi for a guide to the emergency response in the presentation information generating process, and transmits the presentation information PN* or the presentation information PNi to the head mounted display 100.

The step management unit 365 checks a state of the patient in step S312. The detail is the same as illustrated in step S304. A time period, for which a state of the patient is assumed to be stabilized by the emergency response, is preferably placed between step S310 and step S312.

In step S314, the step management unit 365 determines whether the series of steps being currently guided to the user are appropriate. Specifically, the step management unit 365 determines whether the entire medical apparatus information received in step S312 satisfies the "condition" stored in the emergency response information 387. When the entire medical apparatus information does not satisfy the condition (step S314: YES), the step management unit 365 estimates that the series of steps being currently guided to the user are appropriate, and the step management unit 365 transfers the process to step S302. Thereafter, in step S302, the step management unit 365 acquires the next step from the series of steps acquired in step S300, and transmits the next step to the generation unit 360b. In addition, the step management unit 365 checks a state of the patient, and repeatedly executes the aforementioned processes.

In this manner, the step management unit 365 repeatedly acquires the plural pieces of medical apparatus information, and changes the series of steps to be transmitted to the generation unit based on the plural pieces of latest medical apparatus information. For this reason, the information processing apparatus 300b can change a series of steps to be displayed on the plurality of head mounted displays 100a to 100n in real time based on the plural pieces of medical apparatus information that are acquired from the plurality of medical apparatuses.

In contrast, when at least one piece of medical apparatus information satisfies the condition (step S306: YES), the step management unit 365 estimates that the series of steps being currently guided to the user are appropriate, and transfers the process to step S316. In step S316, the step management unit 365 transmits to the generation unit 360b a guide that a state of the patient is bad, and thus the series of steps being currently guided to the user are assumed not to be appropriate. The aforementioned process is executed in the same manner when the presentation information generating process is executed not only in the first mode but also in the second mode. When the generation unit 360b receives the guide that the series of steps being currently guided to the user are not appropriate, the generation unit 360b generates the presentation information PN* or the presentation information PNi so as to guide the user to the fact that the series of steps are not appropriate, and the generation unit 360b transmits the presentation information PN* or the presentation information PNi to the head mounted display 100 in the presentation information generating process. Thereafter, the step management unit 365 stops transmitting the subsequent steps, and ends the process.

In step S310, the step management unit 365 adds a "new step" to "the series of predetermined steps" by transmitting the emergency response based on the acquired medical apparatus information to the generation unit 360b. However, in step S310, the step management unit 365 may execute a "removal of part of steps" or a "replacement of part of steps" with respect to "the series of predetermined steps". For example, when the step to be removed or the step to be replaced is stored as the "emergency response" in the emergency response information 387, the removal of part of steps or the replacement of part of steps can be realized. In the embodiment, the following is collectively referred to as "a change of series of steps" the addition of a new step (the removal of part of steps, or the replacement of part of steps) illustrated in step S310, and the stop of transmission of steps illustrated in step S316.

As described above, in the information processing apparatus 300b of Third Embodiment, the step management unit 365 transmits to the generation unit 360b the information on a series of predetermined steps, and the generation unit 360b generates the presentation information PN* and PNi which contain the received steps. For this reason, the information processing apparatus 300b can display a series of predetermined steps on the plurality of head mounted displays 100a to 100n (the image display apparatuses) connected to the information processing apparatus 300b. In addition, the step management unit 365 changes a series of steps to be transmitted based on plural pieces of medical apparatus information acquired by the first input/output units 311 to 31n (the acquisition units). For this reason, the information processing apparatus 300b can change a series of steps to be displayed on the plurality of head mounted displays 100a to 100n based on the plural pieces of medical apparatus information acquired from the plurality of medical apparatuses. As a result, it is possible to provide the information processing apparatus 300b that can flexibly change the series of predetermined steps based on the medical apparatus information, and can guide the users of the head mounted displays 100a to 100n through the steps.

Furthermore, in the first mode, the step management unit 365 of the information processing apparatus 300b of Third Embodiment transmits, to the generation unit 360b, a series of steps for the user of the head mounted display 100 (that is, the specific image display apparatus), the inter-apparatus relationship of which is a "master" in the management table 382. For this reason, the information processing apparatus 300b can display "a series of common steps for the user of the specific image display apparatus" on the plurality of head mounted displays 100a to 100n (the image display apparatuses) in the first mode. In the second mode, the step management unit 365 transmits a series of steps to the generation unit 360b based on a role of each user of the plurality of head mounted displays 100a to 100n. For this reason, the information processing apparatus 300b can individually display "the series of steps based on the role of each user of the image display apparatus" on the plurality of head mounted displays 100a to 100n in the second mode.

D. Modification Examples

In each embodiment described above, a part of the configuration realized by hardware may be replaced with software. In contrary, a part of the configuration realized by software may be replaced with hardware. In addition, the following modifications can be also made to the embodiments.

Modification Example 1

The configuration of the information processing system is illustrated in each embodiment described above. However, the configuration of the information processing system can be arbitrarily determined insofar as the arbitrarily determined configuration does not depart from the spirit of the invention. For example, it is possible to add, remove, or convert the apparatuses of the information processing system. It is possible to change a configuration of a network of the apparatuses of the information processing system.

For example, the management table, the invisible part information, and the operation record of the information processing apparatus may be stored in the database OD connected to the in-hospital LAN. The provision of the database OD is not limited to the hospital, and the database OD may be provided on the outside (for example, a cloud server that is provided outside the hospital) via the Internet INT.

Modification Example 2

The configuration of the information processing apparatus is illustrated in each embodiment described above. However, the configuration of the information processing apparatus can be arbitrarily determined insofar as the arbitrarily determined configuration does not depart from the spirit of the invention. For example, it is possible to add, remove, or convert each configuration part.

For example, the information processing apparatus may include various input devices such as a touch panel, an input button, a keyboard, a mouse, a microphone, and a camera. Similarly, the information processing apparatus may include various output devices such as a display, an indicator, and a printer so as to output a simple log on an operation.

For example, in each embodiment, the CPU deploys a computer program stored on the ROM or the hard disk on the RAM, and executes the computer program. Accordingly, each function of the generation unit and the second input/output unit (the presentation units) is realized. However, the functions may be realized using an ASIC (Application Specific Integrated Circuit) that is designed so as to realize the functions.

For example, the information processing apparatus is configured to include a display. In addition, the generation unit of the information processing apparatus may display the combined information generated in the combined information generating process on the display of the information processing apparatus. In this manner, a user in the vicinity of the information processing apparatus can understand content displayed on the entirety of the head mounted displays (the image display apparatuses) at a glance, and it is convenient.

Modification Example 3

The configuration of the head mounted display is illustrated in each embodiment described above. However, the configuration of the head mounted display can be arbitrarily determined insofar as the arbitrarily determined configuration does not depart from the spirit of the invention. For example, it is possible to add, remove, or convert each configuration part. For example, the control unit and the image display unit may be connected via a wireless signal transmission path of a wireless LAN, infrared ray communication, Bluetooth, or the like. For example, a primary battery, a fuel cell, a solar cell, a thermal cell, or the like may be adopted as the power supply.

In each embodiment described above, the allocation of the configuration elements to the control unit and the image display unit is only an example, and can be adopted in various forms. For example, the following forms may be adopted. (i) A form in which the control unit is equipped with processing functions such as a CPU and a memory, and the image display unit is equipped with only a display function; (ii) A form in which both control unit and image display unit are equipped with processing functions such as a CPU and a memory; (iii) A form in which the control unit and the image display unit are integrated together (for example, a form in which the image display unit contains the control unit, and functions as an eyeglass type wearable computer); (iv) A form in which a smart phone or a portable game machine is used instead of the control unit; and (v) A form in which the control unit and the image display unit are configured to be wirelessly communicable and wirelessly chargeable, and thus a cable is removed.

For example, the input information acquisition unit may acquire an operation input from the user using various methods other than the methods illustrated in the embodiments. For example, the input information acquisition unit may acquire an operation input via a foot switch (a switch that is operated by the feet of the user). For example, the image display unit may be provided with a visual line detecting unit such as an infrared sensor, and a visual line of the user may be detected. Accordingly, the input information acquisition unit may acquire an operation input via a command associated with a movement of the visual line. For example, a camera may be used to detect a gesture of the user, and the input information acquisition unit may acquire an operation input via a command associated with the gesture. At the detection of the gesture, it is possible to mark a fingertip of the user, a finger ring attached to the hands of the user, a medical instrument or the like held by the hands of the user for the detection of a movement. When the input information acquisition unit can acquire an operation input via the foot switch or the visual line, the input information acquisition unit can easily acquire the operation input from the user even in a medical location where it is difficult for the user to free up the hands.

For example, in the embodiments, the head mounted display is the binocular transmissive head mounted display, but the head mounted display may be a monocular head mounted display. The embodiment may be configured to adopt a non-transmissive head mounted display through which an outside scene is prevented from being seen when the user wears the head mounted display. The embodiments adopt the head mounted display, the image display unit of which the user wears like eyeglasses. However, the head mounted display may adopt the image display unit with other shape, for example, the image display unit that the user wears like a hat. An earphone or a headband earphone may be adopted as the earphone, or the earphone may be omitted. Furthermore, for example, the embodiment may be configured to adopt a head-up display (HUD) mounted on a vehicle such as an automobile or an airplane. In addition, the embodiment may adopt the head mounted display that is built in a body protection tool such as a helmet.

Figure 23A:
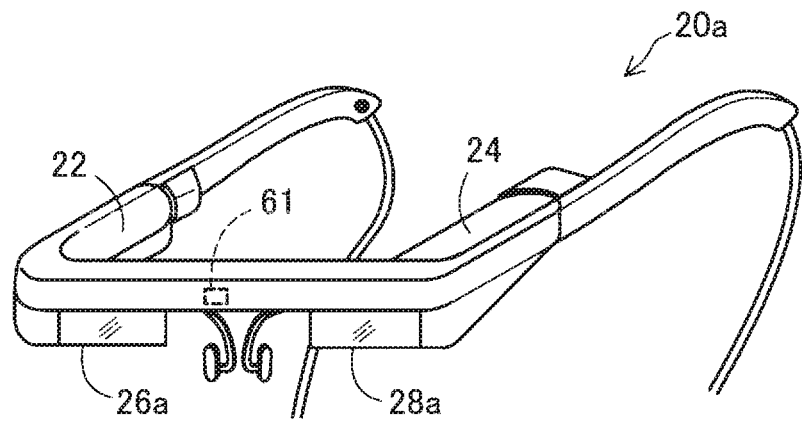
FIG. 23A illustrates a view showing an external configuration of each head mounted display in modification examples.
Figure 23B:
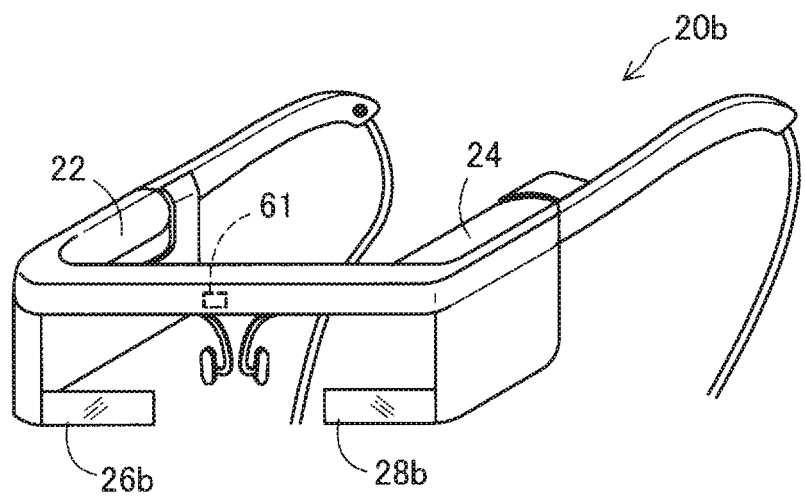
FIG. 23B illustrates a view showing an external configuration of each head mounted display in modification examples.

FIGS. 23A and 23B illustrates views showing an external configuration of each head mounted display in modification examples. In the example illustrated in FIG. 23A, an image display unit 20a includes a right optical image display unit 26a instead of the right optical image display unit 26, and includes a left optical image display unit 28a instead of the left optical image display unit 28. The right optical image display unit 26a is formed to be smaller than the optical member in First Embodiment, and is obliquely arranged above the right eye of a user when the user wears the head mounted display. Similarly, the left optical image display unit 28a is formed to be smaller than the optical member in First Embodiment, and is obliquely arranged above the left eye of the user when the user wears the head mounted display. In the example illustrated in FIG. 23B, an image display unit 20b includes a right optical image display unit 26b instead of the right optical image display unit 26, and includes a left optical image display unit 28b instead of the left optical image display unit 28. The right optical image display unit 26b is formed to be smaller than the optical member in First Embodiment, and is obliquely arranged below the right eye of a user when the user wears the head mounted display. The left optical image display unit 28b is formed to be smaller than the optical member in First Embodiment, and is obliquely arranged below the left eye of the user when the user wears the head mounted display. In this manner, it is satisfactory for the optical image display unit to be arranged in the vicinity of the eyes of the user. A size of the optical member, which forms the optical image display unit, may be also arbitrarily determined. It is possible to realize the head mounted display in such a manner that only parts of the eyes of the user are covered with the optical image display units, in other words, the eyes of the user are not completely covered with the optical image display units.

For example, in each embodiment described above, the display driving unit is configured to include the backlight, the backlight control unit, the LCD, the LCD control unit, and the projection optical system, but the configuration form is only an example. In addition to or instead of the configuration parts, the display driving unit may include configuration parts so as to realize other display driving method. For example, the display driving unit may emit image light using a front light method or a reflection method. For example, the display driving unit may be configured to include an organic EL (Organic Electro-Luminescence) display, an organic EL control unit, and a projection optical system. For example, the display driving unit can also use a digital micromirror device or the like instead of the LCD. For example, the invention is also applicable to a laser retinal projection head mounted display apparatus.

Modification Example 4

The embodiment illustrates an example of the presentation information generating process. However, the procedures of the presentation information generating process are only examples, and various modifications can be made to the procedures. For example, a part of steps may be omitted, or additionally, other steps may be added. The steps may be executed in a changed order.

For example, the invisible part information described in the embodiments is assumed to be a two-dimensional image. However, the medical apparatus capable of photographing a three-dimensional invisible part image may be connected.

The invisible part information stored in the external storage apparatus may be a three-dimensional model produced from a plurality of images photographed by an image photographing device. When the three-dimensional invisible part information is used, the generation unit renders a three-dimensional model prior to generating the presentation information. The generation unit generates the presentation information using the rendered image. In this manner, it is possible to see information in various directions, which does not appear in an external appearance of a target object.

For example, when the presentation information generating process is executed in the first mode, the generation unit may generate plural pieces of common presentation information. Specifically, for example, the head mounted displays, which are respectively connected to the second input/output units, are divided into an m (m is an integer equal to or greater than 1) number of groups. In addition, the generation unit may generate common presentation information for each group like common presentation information for a first group, . . . common presentation information for an m-th group.

For example, when the presentation information generating process (the initial process) is executed in the second mode, the initial process is executed in serial using the variable i with respect to the plurality of head mounted displays that are respectively connected to the second input/output units. However, the initial process may be executed in parallel with reference to the plurality of head mounted displays that are respectively connected to the second input/output units.

For example, in the presentation information generating process executed in the second mode, either the initial process or the individual process may be omitted. The initial process may not be executed immediately after the presentation information generating process is started in the second mode. The same process as the initial process may be appropriately executed based on a request from a user or other applications.

For example, in both first and second modes, the image contained in the presentation information may be enlarged or reduced based on a request from a user to be displayed as the virtual image VI on the head mounted display. Similarly, the head mounted display may not display the image contained in the presentation information based on a request of a user, and the head mounted display may convert a color of the image contained in the presentation information. When a user inputs a request via a voice input method using a microphone, it is possible to considerably improve convenience of each user when the head mounted display is used in a medical location where it is difficult for the user to operate the head mounted display by the hands.

Modification Example 5

The embodiment illustrates an example of the combined information generating process. However, the procedures of the combined information generating process are only an example, and various modifications can be made to the procedures. For example, a part of may be omitted, or other steps may be further added. The steps may be executed in a changed order.

For example, the generation unit may allow the to-be-generated combined information to contain information other than a reduced image in the presentation information. For example, the combined information may contain the following listed information.

A string of letters or an image for identifying the head mounted display to which the presentation information is supplied.

A string of letters or an image for indicating a managerial position of a user of the head mounted display to which the presentation information is supplied.

The medical apparatus information of the medical apparatus.

Data stored in the in-hospital database.

Data stored in the invisible part information.

Data stored in the invisible part information.

The medical apparatus information of the medical apparatus the display unit of which it is difficult for the user to see.

For example, the generation unit may receive a request for combined information from only a specific head mounted display. For example, the specific head mounted display is a master head mounted display, or a head mounted display a user of which takes a specific role.

Modification Example 6

The embodiment illustrates an example of the step management process. However, the procedures of the step management process are only examples, and various modifications can be made to the procedures. For example, a part of steps may be omitted, or other steps may be further added. The steps may be executed in a changed order.

For example, instead of the addition of a new step (the removal of a part of steps or the replacement of a part of steps) illustrated in step S310, or in addition to the addition, the removal, or the replacement of a new step, the embodiment may adopt a configuration in which the doctor PR in an external facility can present a second opinion via a telephone call with the doctor PR (refer to FIG. 19).

For example, any one of the following may be omitted: the addition of a new step (the removal of a part of steps or the replacement of a part of steps) illustrated in step S310, and the stop of transmission of steps illustrated in step S316.

For example, "a series of predetermined steps" are determined by an operating surgeon, other doctors, or the like. The step management unit may be configured to suggest a series of steps, which have to be a candidate for "the series of predetermined steps" (if necessary, plural pairs of series of steps), to a user of the head mounted display. In this case, for example, the step management unit can derive the candidate by retrieving the step information based on the medical apparatus information that is acquired in advance.

For example, the step management process may handle only one of the presentation information generating process in the first mode and the presentation information generating process in the second mode.

Modification Example 7

The embodiments illustrate an example of the common video specification, the management table, the step information, and the emergency response information. However, the detailed descriptions are only examples, and various medications can be made. For example, it is possible to add, remove, or change a field (an item). The management table may be divided into a plurality of tables, and may be standardized.

For example, voice prints of the users of the head mounted displays may be stored in the management table instead of the identifiers for individually identifying the head mounted displays, or along with the identifiers. Accordingly, the information processing apparatus can acquire the inter-apparatus relationship, the role, and the video specification of the head mounted display of the user based on the voice print of the user acquired via a microphone, and the information processing apparatus can execute the presentation information generating process.

For example, information (for example, IP addresses, MAC addresses, and encryption keys of the head mounted displays) used in communication between the head mounted display and the information processing apparatus may be further stored in the management table in association with the identifiers of the head mounted displays. Instead of "the video specification" that indicates a pattern of the video signal specification, an actual video specification (that is, the same item as that stored in the common video specification) adopted in each head mounted display may be stored in the management table.

For example, the management table stores the inter-apparatus relationship, the role, and the video specification for each identifier of the head mounted display. However, a "user ID" may be assigned to each user, and the inter-apparatus relationship, the role, and the video specification may be stored for each user ID in the management table.

For example, the "emergency response", which is stored in the emergency response information in advance, is a single response. However, a plurality of responses may be stored in the emergency response. The step management unit may guide the user of the image display apparatus through the plurality of responses. In this manner, the user of the image display apparatus can select an emergency response from the plurality of emergency responses, which is considered to be the most suitable based on his or her experience or situation. As a result, it is possible to further improve convenience of the information processing apparatus.

Modification Example 8

The invention is not limited to the embodiments, the examples, and the modification examples described above. The invention can be realized in various configurations insofar as the various configurations do not depart from the spirit of the invention. For example, it is possible to appropriately replace or combine together technical characteristics in the embodiments, the examples, and the modification examples, which respectively correspond to technical characteristics of the aspects described in the summary of the invention so as to solve a part or the entirety of the problems, or to achieve a part or the entirety of the advantages. Unless the technical characteristics are described as being essential in this document, the technical characteristics can be appropriately removed.

REFERENCE SIGNS LIST

10: control unit
20: image display unit
22: right display driving unit
24: left display driving unit
26: right optical image display unit
28: left optical image display unit
32: right earphone
34: left earphone
40: cable
51: transmitting unit
52: transmitting unit
53: receiving unit
54: receiving unit
61: camera (image acquisition unit)
110: input information acquisition unit
100: head mounted display (image display apparatus, head mounted display apparatus)
120: storage unit
130: power supply
140: CPU
160: image processing unit
170: voice processing unit
180: interface
190: display control unit
201: right backlight control unit
202: left backlight control unit
211: right LCD control unit
212: left LCD control unit
221: right backlight
222: left backlight
241: right LCD
242: left LCD
251: right projection optical system
252: left projection optical system
261: right light guide plate
262: left light guide plate
300: information processing apparatus
310: first input/output unit
311 to 31$n$: first input/output unit (acquisition unit)
320: ROM
330: RAM
340: communication interface
350: CPU
360: generation unit
365: step management unit
370: second input/output unit (presentation unit)
371 to 37$n$: second input/output unit
380: external storage apparatus
381: common video specification
382: management table (role storage unit and inter-apparatus relationship storage unit)
383: invisible part information
384: operation record
385: operation mode
386: step information
387: emergency response information
500: medical apparatus
501 to 50$n$: medical apparatus
700: display
1000: information processing system
OA: external device
PC: personal computer
OD: database
VI: virtual image
PN: presentation information
JN: combined information
VR: visual field
PR: doctor
MP1: position
UP1: current position
CP1: medical apparatus information

The invention claimed is:

1. An information processing apparatus comprising:
a processor configured to:
detect a connection to a first image display apparatus that captures an outside scene and a connection to a second image display apparatus that captures the outside scene;
acquire first medical apparatus information from a first medical apparatus and second medical apparatus information from a second medical apparatus different from the first medical apparatus;

generate a first image based on the first medical apparatus information and a second image based on the second medical apparatus information;

detect an object from the outside scene;

acquire a first distance from the first image display apparatus to the object and a second distance from the second image display apparatus to the object;

execute a first mode in which both of the first image display apparatus and the second image display apparatus display the first image, or a second mode in which the first image display apparatus displays the first image and the second image display apparatus displays the second image;

switch from the second mode to the first mode when processor an instruction from the first image display apparatus is accepted by the processor; and in the first mode, cause the first image display apparatus to display the first image at a first size that is greater than a second size of the first image displayed at the second image display apparatus, when the first distance is smaller than the second distance.

2. An information processing apparatus according to claim 1, wherein
each of the first image display apparatus and the second image display apparatus is a head mounted display.

3. An information processing apparatus according to claim 1, wherein
the processor is configured to:
detect an edge of the object, and
cause the first image display apparatus to display an edge of the first image to overlap with the edge of the object.

4. An information processing apparatus according to claim 1, wherein
the processor is configured to cause the first image display apparatus to display the first image at a third size that is smaller than the first size at a third distance that is longer than the first distance.

5. An information processing apparatus according to claim 1, wherein
the processor is configured to:
detect an orientation of the object; and
cause the first image display apparatus to change an orientation of the first image based on the orientation of the object.

6. An information processing apparatus according to claim 1, wherein
the processor is configured to:
detect a first marker that is attached to the object, and
cause the first image display apparatus to change an orientation of the first image based on the first marker of the object.

7. An information processing apparatus according to claim 6, wherein
the first image includes a second marker, and
the processor is configured to cause the first image display apparatus to display the second marker included with the first image to overlap with the first marker.

8. An information processing apparatus according to claim 1, wherein
the processor is further configured to:
acquire a brightness of the outside scene; and
convert a color of the first image a complementary color of the color based on the brightness of the outside scene.

9. An information processing apparatus according to claim 1, wherein
the processor is further configured to:
acquire a color of the outside scene; and
convert a color of the first image to a complementary color of the color of the outside scene.

10. An information processing apparatus according to claim 1, wherein
the first image is a three-dimensional image.

11. A method for controlling an information processing apparatus, the method comprising:
detecting a connection to a first image display apparatus that captures an outside scene and a connection to a second image display apparatus different from the first image display apparatus;
acquiring first medical apparatus information from a first medical apparatus and second medical apparatus information from a second medical apparatus different from the first medical apparatus;
generating a first image based on the first medical apparatus information and a second image based on the second medical apparatus information;
detecting an object from the outside scene;
acquiring a first distance from the first image display apparatus to the object and a second distance from the second image display apparatus to the object; and
executing a first mode in which both of the first image display apparatus and the second image display apparatus display the first image, or a second mode in which the first image display apparatus displays the first image and the second image display apparatus displays the second image;
switching from the second mode to the first mode when an instruction from the first image display apparatus is accepted; and
in the first mode, causing the first image display apparatus to display the first image at a first size that is greater than a second size of the first image displayed at the second image display apparatus, when the first distance is smaller than the second distance.

12. The method according to claim 11, further comprising:
detecting an orientation of the object; and
causing the first image display apparatus to change an orientation of the first image based on the orientation of the object.

* * * * *